United States Patent
Myers et al.

(10) Patent No.: US 7,536,214 B2
(45) Date of Patent: May 19, 2009

(54) DYNAMIC $STO_2$ MEASUREMENTS AND ANALYSIS

(75) Inventors: Dean E. Myers, Stewart, MN (US); Jeffrey C. Jones, Hutchinson, MN (US)

(73) Assignee: Hutchinson Technology Incorporated, Hutchinson, MN (US)

( * ) Notice: Subject to any disclaimer, the term of this patent is extended or adjusted under 35 U.S.C. 154(b) by 604 days.

(21) Appl. No.: 11/259,382

(22) Filed: Oct. 26, 2005

(65) Prior Publication Data

US 2007/0093701 A1  Apr. 26, 2007

(51) Int. Cl.
A61B 5/1455 (2006.01)

(52) U.S. Cl. .................. 600/323; 600/324; 600/335

(58) Field of Classification Search ............. 600/322, 600/323, 324, 335
See application file for complete search history.

(56) References Cited

U.S. PATENT DOCUMENTS

| | | | |
|---|---|---|---|
| 3,439,267 A | 4/1969 | Coulter et al. | |
| 3,654,916 A | 4/1972 | Neilson | |
| 3,686,486 A | 8/1972 | Coulter et al. | |
| 3,825,008 A | 7/1974 | Shook | |
| 4,222,389 A | 9/1980 | Rubens | |
| 4,294,261 A | 10/1981 | Baker et al. | |
| 4,463,762 A | 8/1984 | Rubens | |
| 4,513,751 A | 4/1985 | Abe et al. | |
| 4,768,516 A | 9/1988 | Stoddart et al. | |
| 4,883,055 A | 11/1989 | Merrick | |
| 4,927,264 A | 5/1990 | Shiga et al. | |
| 5,199,439 A | 4/1993 | Zimmerman et al. | |
| 5,267,563 A | 12/1993 | Swedlow et al. | |
| 5,282,467 A | 2/1994 | Piantadosi et al. | |
| 5,372,135 A | 12/1994 | Mendelson et al. | |
| 5,638,816 A | 6/1997 | Kiani-Azarbayjany et al. | |
| 5,671,734 A | 9/1997 | Pugh | |
| 5,771,891 A | 6/1998 | Gozani | |
| 5,830,133 A * | 11/1998 | Osten et al. | 600/322 |
| 5,865,736 A * | 2/1999 | Baker et al. | 600/323 |
| 5,916,154 A | 6/1999 | Hobbs et al. | |

(Continued)

FOREIGN PATENT DOCUMENTS

WO    0077495 A1   12/2000

OTHER PUBLICATIONS

Kragelj et al., "Parameters of Postocclusive Reactive Hyperemia Measured by Near Infrared Spectroscopy in Patients with Peripheral Vascular Disease and In Healthy Volunteers," Annals of Biomedical Engineering, vol. 29, pp. 311-320, 2001.

(Continued)

Primary Examiner—Eric F Winakur
Assistant Examiner—Etsub D Berhanu
(74) Attorney, Agent, or Firm—Faegre & Benson LLP

(57) ABSTRACT

A method of analyzing a patient's tissue oxygenation capabilities includes measuring a tissue chromophore whose light absorption properties depend on the oxygenation state of the tissue and generating data representative of tissue oxygenation before, during and after a controlled ischemia event. From this data characterizing data, including ischemia onset slope, ischemia onset response time, ischemia recovery slope, ischemia recovery response time or hyperemia is automatically determined. This characterizing data is related to corresponding characterizing data determined from a control population. The relationship may be displayed on a graphical display.

51 Claims, 17 Drawing Sheets

U.S. PATENT DOCUMENTS

| | | | |
|---|---|---|---|
| 5,931,779 | A | 8/1999 | Arakaki et al. |
| 5,941,820 | A | 8/1999 | Zimmerman |
| 6,063,026 | A | 5/2000 | Schauss et al. |
| 6,222,189 | B1 | 4/2001 | Misner et al. |
| 6,400,972 | B1 | 6/2002 | Fine |
| 6,416,479 | B1 | 7/2002 | Seidman |
| 6,519,485 | B2 | 2/2003 | Weismann et al. |
| 6,572,558 | B2 | 6/2003 | Masakov et al. |
| 6,587,704 | B1 | 7/2003 | Fine et al. |
| 6,682,481 | B2 | 1/2004 | McKinley et al. |
| 6,711,424 | B1 | 3/2004 | Fine et al. |
| 6,718,189 | B2 | 4/2004 | Rohrscheib et al. |
| 6,754,516 | B2 | 6/2004 | Mannheimer |
| 6,776,764 | B2 | 8/2004 | Pinsky |
| 6,933,154 | B2 | 8/2005 | Schomacker et al. |
| 7,247,142 | B1 | 7/2007 | Elmandjra |
| 2004/0092809 | A1* | 5/2004 | DeCharms .................. 600/410 |
| 2007/0093701 | A1 | 4/2007 | Myers et al. |

OTHER PUBLICATIONS

Kragelj et al., "Reproducibility of Parameters of Postocclusive Reactive Hyperemia Measured by Near Infrared Spectroscopy and Transcutaneous Oximetry," Annals of Biomedical Engineering, vol. 28, pp. 168-173, 2000.

Pareznik et al., "Improvement of Muscle Tissue Deoxygenation During Stagnant Ischemia in Survivors of Severe Sepsis", Department for Internal Intensive Medicine, General Hospital Celje, Celje, Slovenia, Hutchinson Technology Incorporated BioMeasurement Division, Presentation at the 17th ESICM Annual Congress, Berlin, Germany, Oct. 10-13, 2004, 4 pages.

Krug et al., "Optical Tissue Measurement for Determination of Local Blood Flow, Local Oxygen Saturation and Local Hemoglobin Quantity, Microcirculation in Vivo", *Optical Tissue Messure,* Cephalon, Copyright 2004, 11 pages.

Casavola et al., "Blood Flow and Oxygen Consumption with Near-Infrared Spectroscopy and Venuous Occlusion: Spatial Maps and the Effect of Time and Pressure of Inflation", *Journal of Biomedical Optics* vol. 5 No. 3, pp. 269-276, Jul. 2000.

Piantadosi, "Near Infrared Spectroscopy: Principles and Application to Noninvasive Assessment of Tissue Oxygenation", Division of Respiratory Diseases and Critical Care Medicine, Duke University Medical Center, Durham, North Carolina, W.B. Saunders Company, pp. 308-318, Dec. 1989.

Miller et al., "Circulatory Responses to Voluntary and Electrically Induced Muscle Contractions in Humans", *Physical Therapy* vol. 80 No. 1, pp. 52-59, Jan. 2000.

Van Beekvelt et al., "Blood Flow and Muscle Oxygen Uptake at the Onset and End of Moderate and Heavy Dynamic Forearm Exercise", *American Journal of Physiology—Regulatory, Integrative and Comparative Physiology* vol. 280 Issue 6, pp. R1741-R1747, Jun. 2001.

Francheschini et al., "Noninvasive Optical Method of Measuring Tissue and Arterial Saturation: An Application to Absolute Pulse Oximetry of the Brain", *Optics Letters* vol. 24 No. 12, pp. 829-831, Optical Society of America, Jun. 15, 1999.

Takala, "Assessment of Tissue Hypoxia 12 RC 2", European Society of Anaesthesiologists, Vienna, Apr. 1, 2000, 6 pages.

Goldman et al., "Effect of Sepsis on Skeletal Muscle Oxygen Comsumption and Tissue Oxygenation: Interpreting Capillary Oxygen Transport Data Using a Mathematical Model", *American Journal of Physiology—Heart and Circulatory Physiology* vol. 287, pp. H2535-H2544, Aug. 19, 2004.

Sair et al., "Tissue Oxygenation and Perfusion in Patients with Systemic Sepsis", Unit of Critical Care, Imperial College School of Medicine and Royal Brompton Hospital, London, UK, *Critical Care Medicine* 29(7), Jul. 2001, pp. 1343-1349.

Bauer et al., "Impaired Muscle Oxygen Use at Onset of Exercise in Peripheral Arterial Disease", University of Colorado Health Sciences Center, *Journal of Vascular Surgery* vol. 40 No. 3, Sep. 2004, pp. 488-493.

De Blasi et al., "Noninvasive Measurement of Forearm Blood Flow and Oxygen Consumption by Near-Infrared Spectroscopy", *Journal of Applied Physiology* 76(3), pp. 1388-1393, Copyright 1994.

De Blasi et al., "$O_2$ Consumption—$O_2$ Delivery Relationship and Arteriolar Resistance in the Forearm of Critically Ill Patients Measured by Near Infrared Spectroscopy", *Shock* vol. 6 No. 5, pp. 319-325, Nov. 1996.

Girardis et al., "Muscle Perfusion and Oxygen Consumption by Near-Infrared Spectroscopy in Septic-Shock and Non-Septic-Shock Patients", *Intensive Care Med* 29, pp. 1173-1176, May 2003.

Casavola et al., "Near-Infrared Spectroscopy and the Tilting Table Protocol: A novel Method to Study the Blood Flow and the Oxygen Consumption in Tissues", Part of the SPIE Conference on Optical Tomography and Spectroscopy of Tissue III, San Jose, California, Jan. 1999, SPIE vol. 3597, pp. 685-692.

De Blasi et al., "Noninvasive Measurement of Forearm Oxygen Consumption During Exercise by Near Infrared Spectroscopy", *Oxygen Transport to Tissue XV,* Plenum Press, New York, pp. 685-692, 1994.

Ferrari et al., "Oxidative Metabolism in Muscle", *Philosophical Transactions of the Royal Society London B 352,* pp. 677-683, 1997.

De Backer et al., "Microvascular Blood Flow is Altered in Patients with Sepsis", *American Journal of Respiratory and Critical Care Medicine* vol. 166, pp. 98-104, 2002.

Neviere et al., "Skeletal Muscle Microvascular Blood Flow and Oxygen Transport in Patients with Severe Sepsis", *American Journal of Respiratory and Critical Care Medicine* vol. 153, pp. 191-195, 1996.

* cited by examiner

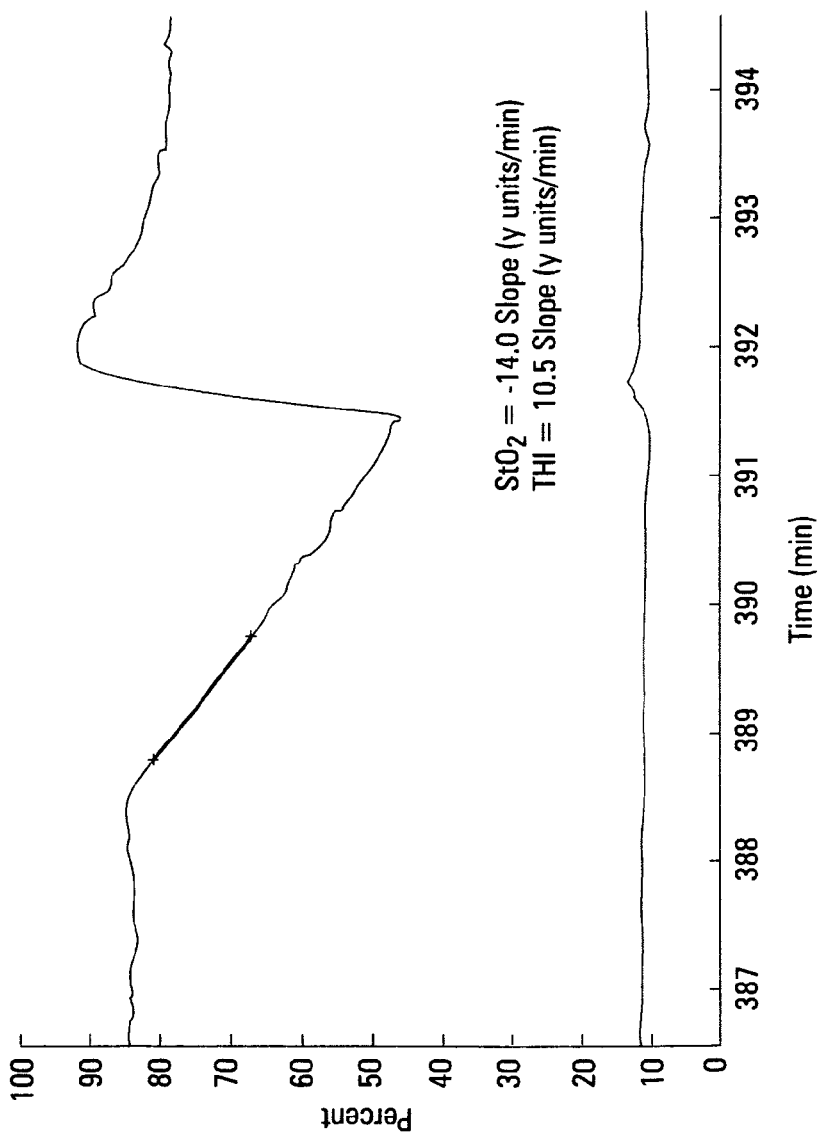

Ischemia Recovery Slope Adjusted for Total Amount (High) of Hemoglobin in the Tissue $StO_2$ = 156.1 Slope (y units/min)
THI = 11.5 Slope (y units/min)

Average THI is 11.5 for $StO_2$ slope calculation during ischemia recovery. The $StO_2$ slope value is 156.1 $StO_2$ units per minute.

DYNAMIC STO$_2$ MEASUREMENTS AND ANALYSIS

TECHNICAL FIELD

The present invention relates to a method for acquiring and characterizing data relating to tissue oxygenation.

BACKGROUND OF THE INVENTION

Septic shock is the most serious complication of sepsis, a disorder that occurs when the body responds to an infection. Shock, including septic shock, is characterized by blood flow that is inadequate to meet tissue oxygen demand. Prompt recognition of inadequate organ and tissue blood flow, known as hypotension and hypoperfusion, is essential for timely treatment and improved outcome in shock related disorders. Thus, tissue oxygenation may be monitored as a means of monitoring and diagnosing shock, sepsis and other types of infections, as well as monitoring a patient's overall health.

Previously, there were two basic kinds of oxygenation measurements—hemoglobin oxygen saturation in the blood and transcutaneous partial pressure of oxygen. Hemoglobin oxygen saturation in the blood ($SO_2$, $SaO_2$, $SpO_2$), expressed as a percent, is the oxygen present on the hemoglobin in circulating blood divided by the total possible oxygen that could be carried by the hemoglobin. Transcutaneous partial pressure of oxygen ($PO_2$) measures the amount of oxygen drawn to the skin's surface by a heated sensor and provides an estimate of arterial partial pressure of oxygen.

$StO_2$ is the quantification of the ratio of oxygenated hemoglobin to total hemoglobin in the microcirculation of skeletal muscle, and is an absolute number. The measurement of $StO_2$ is taken with a noninvasive, fiber optic light that illuminates tissues below the level of the skin. One way to illuminate tissue below the level of the skin is known as near infrared spectroscopy (NIRS), which uses specific, calibrated wavelengths of near infrared light to noninvasively illuminate the tissue below the skin. These wavelengths of light scatter in the tissue and are absorbed differently dependent on the amount of oxygen attached to hemoglobin in the arterioles, venules, and capillaries. Light that is not absorbed is returned as an optical signal and analyzed to produce a ratio of oxygenated hemoglobin to total hemoglobin, expressed as % $StO_2$.

In practice, near infrared light penetrates tissues such as skin, bone, muscle and soft tissue where it is absorbed by chromophores (hemoglobin and myoglobin) that have absorption wavelengths in the near infrared region (approximately 700-1000 nm). These chromophores vary in their absorbance of NIRS light, depending on changes in the oxygenation state of the tissue. Complex algorithms differentiate the absorbance contribution of the individual chromophores.

While $StO_2$ correlates well with other accepted means of measuring oxygen saturation, $StO_2$ measurement differs from the $SpO_2$ near infrared measurement provided by pulse oximetry. Pulse oximetry measures the systemic oxygen saturation of arterial blood, and requires a pulsatile flow. In contrast, $StO_2$ measures the oxygen saturation of local muscle tissue and does not require a pulsatile flow.

Furthermore, pulse oximetry measures hemoglobin oxygen saturation prior to delivery to the microcirculation where oxygen is exchanged with the cells. $SpO_2$ is therefore a systemic measure and is fairly constant regardless of whether the measurement site is the earlobe, finger, or big toe. Thus, while measurements of $StO_2$ will change as the conditions of supply and consumption change at the measurement site, measurements of $SpO_2$ will not.

Finally, while near infrared spectroscopy can be used to measure oxygenation at various depths of tissue—skin, subcutaneous tissue, and muscle, transcutaneous $PO_2$ measures the partial pressure of oxygen in the skin only.

It is known that noninvasive hemodynamic monitoring may be able to predict outcome in trauma, including shock and sepsis. While methods of making such predictions in relation to pulse oximetry and transcutaneous $PO_2$ are widely known, such methods are not available in relation to $StO_2$. Furthermore, transforming a measurement of tissue oxygenation into a convenient and usable format relating to a patient's oxygenation capabilities is time consuming and tedious. Complex algorithms may be necessary to transform the data, and comparison of both raw data and transformed data to normal or standardized values for evaluating the patient's condition may require charts or other tools.

What is needed, then, is an improved method of using tissue oxygenation data, including $StO_2$ data, to quickly and easily inform a physician about a patient's tissue oxygenation capabilities. This information may then be used by the physician to diagnose and monitor conditions of shock, sepsis and infection as well as to predict outcome in patients suffering from such conditions.

SUMMARY OF THE INVENTION

In one embodiment, the present invention is a method for analyzing data related to tissue oxygenation. An initial measurement is taken to collect data on a tissue chromophore whose light absorption properties depend on the oxygenation state of the tissue. Blood flow is restricted for a first predetermined period in the region where the initial measurement was made while continuing to measure the tissue chromophore. The blood flow is un-restricted after the first predetermined period while continuing to measure the tissue chromophore. Using the data collected during the measurements, an ischemia start point and an ischemia end point of the first predetermined period are automatically determined within the data.

In another embodiment, the present invention is a method for analyzing a patient's tissue oxygenation capabilities. A tissue chromophore whose light absorption properties depend on the oxygenation state of the tissue is measured and data representative of tissue oxygenation before, during and after a controlled ischemia event is generated. From said data characterizing data related to tissue oxygenation is automatically determined.

In another embodiment, the present invention is an apparatus for analyzing a patient's tissue oxygenation capabilities. The apparatus includes a software program for installation on a processor. The software program is adapted to input data from measurements of a tissue chromophore whose light absorption properties depend on the oxygenation state of the tissue before, during and after a controlled ischemic event and to determine from said data characterizing data related to tissue oxygenation.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 7A is a graph illustrating an ischemia onset slope determination example as percent $StO_2$ versus time in which the patient has a high volume of hemoglobin in the tissue.

Figure 1:
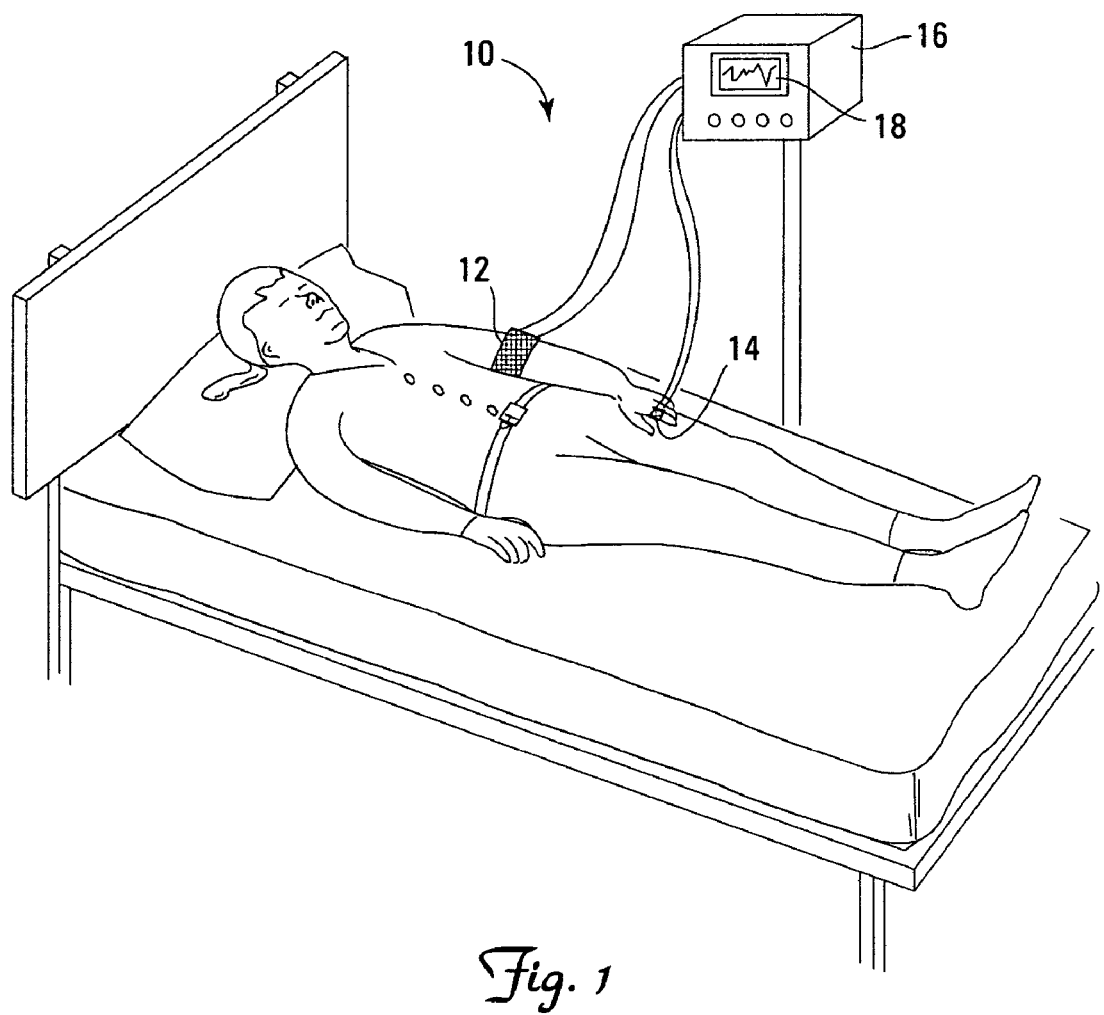
FIG. 1 shows a schematic illustration of a tissue oxygenation monitoring system that can be used in relation to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION OF THE INVENTION

FIG. 1 shows an exemplary system 10 for use in gathering, analyzing and displaying data related to patient tissue oxygenation. The information conveyed by the displayed data may be employed by a physician to monitor in real time a patient's dynamic tissue oxygenation response characteristics.

The system 10 includes a restriction means 12 for restricting blood flow to a tissue region of the patient, a patient sensor 14 for gathering data related to tissue oxygenation of the tissue region, a control module 16 in communication with the sensor 14 for analyzing or characterizing the tissue oxygenation data, and a display 18 for indicating or displaying tissue oxygenation data.

The sensor 14 includes a noninvasive, fiber optic light that illuminates tissues below the level of the skin (not shown). In one embodiment, the sensor 14 employs near infrared spectroscopy (NIRS), which uses specific, calibrated wavelengths of near infrared light to noninvasively illuminate a region of tissue below the skin. These wavelengths of light scatter in the tissue and are absorbed differently depending on the amount of oxygen attached to a tissue chromophore, such as hemoglobin, in the arterioles, venules, and capillaries. Light that is not absorbed is returned to the sensor. Thus, the sensor 14 is able to gather data on a tissue chromophore whose light absorption properties depend on the oxygenation state of the tissue. The returned light may be transmitted as an optical signal and is analyzed to produce a ratio of oxygenated hemoglobin to total hemoglobin, expressed as % $StO_2$. Tissue chromophore data may also be expressed as tissue oxygenation, tissue deoxygenation and/or total amount of hemoglobin in the tissue. An exemplary sensor for use with the present invention is described in U.S. patent application Ser. No. 11/129,935 titled PATIENT INTERFACE FOR SPECTROSCOPY APPLICATIONS, filed on May 16, 2005, the entire disclosure of which is hereby incorporated herein by reference.

The restriction means 12 may be a blood-pressure type cuff, tourniquet or any other means of restricting blood flow to a selected tissue region of the body as is known in the medical arts. The restriction means 12 should be capable of restricting or occluding substantially all of the blood flow to the selected tissue region, including, but not limited to, both arterial and venous blood flow. In one embodiment, the restriction means 12 may exert up to about 50 mmHg of pressure above the patient's systolic blood pressure. Blood flow to the tissue region may thus be entirely or substantially entirely restricted. In another embodiment, the restriction means 12 may exert at least about 10 mmHg of pressure less than the patient's diastolic blood pressure. In this manner, venous blood flow, but not arterial blood flow, will be entirely or substantially restricted. The restriction means 12 may be placed on an arm or leg in such a manner as physicians and nurses are familiar with. The restriction means 12 may be manually operated to restrict and permit blood flow or may be automated and operable under control of the control module 16.

In other embodiments, blood flow to the selected tissue region may be reduced by controlling the temperature of the selected tissue region. For example, it is known that blood flow may be reduced by lower tissue temperature and increased by raising tissue temperature. Thus, the restriction means 12 may be a heating or cooling mechanism fitted over a portion of the patient's anatomy. In still other embodiments, blood flow to the selected tissue region may be reduced by raising the selected tissue region higher than the patient's heart or trunk. This may be accomplished by lifting a portion of the patient's anatomy, as for example by raising the patient's arm, or by raising a portion of the hospital bed to raise the patient's legs.

The sensor 14 may be placed on any location that is located distal or downstream from the restriction means 12 in relation to arterial blood flow. For example, the sensor 14 may be placed on the thenar muscle of the thumb, as is shown in FIG. 1, while the restriction means 12 is located on the upper or lower arm. Alternately, the sensor 14 may be located on the hypothenar, the forearm, the upper arm, the deltoid, the calf, etc., with the restriction means 12 located proximally or upstream therefrom.

Because NIRS is capable of measuring tissue oxygenation levels particular to the localized area of placement of the sensor 14, the sensor 14 may be placed in locations to monitor particular areas of interest. For example, the sensor 14 may be placed over or adjacent to areas of trauma so as to measure tissue oxygenation of the traumatized or healing tissues. The sensor 14 may also be placed over areas where infection is known or suspected to exist. The sensor 14 may also be placed in locations known to be provided with good arterial blood flow or having certain types of tissue which are more easily illuminated by the sensor 14.

The sensor 14 and control module 16 may be provided with a variety of means of communicating with one another. For example, as shown in FIG. 1, the control module 16 and the sensor 14 may be connected to one another and communicate via electrical or optical signals. In other embodiments, the connection between the control module 16 and the sensor 14 is wireless, and the control module 16 and the sensor 14 communicate with radio signals or other "wireless" modes of communication. In addition, the light source for the sensor 14 may be located either in the sensor 14 or remotely from the sensor 14 and optically coupled thereto.

The control module 16 is adapted for controlling the operation of the sensor 14, analyzing data generated by the sensor 14, and communicating data to the display 18. In addition, the control module 16 may be adapted to control operation of the restriction means 12. The control module 16 may thus be adapted to cause the restriction means 12 to restrict blood flow and to permit blood flow. The control module 16 may include a data processor or other means of analyzing data communicated from the sensor 14. Furthermore, the control module 16 and display 18 may be integrated into a single unit, as shown in FIG. 1, or may be separate from one another and/or integrated into other monitoring and display devices. For example, the control module 16 may be integrated into an automatic blood-pressure monitoring device as is commonly found in hospital rooms.

The display 18 may display information relating the measured tissue oxygenation as well as characterizing data based on the measured tissue oxygenation. The display of such information may take a variety of formats. For example, the display 18 may be adapted to display text, graphs or waveforms relating to contemporaneously acquired data, historical data, mean data or any combination thereof. The display 18 may also be adapted to provide instructions as to the use of the system 10 or to display notices or warnings related to the operation and functionality of system 10.

A first method employing the system 10 shown in FIG. 1 to analyze a patient's tissue oxygenation capabilities includes the following steps. The sensor 14 is placed on the skin in a selected region, for example, over the thenar muscle of the hand. The restriction means 12 is positioned on the patient's arm so that upon operation of the restriction means 12 blood flow to the selected tissue region is restricted. An initial measurement is taken by the sensor 14 to collect data on a tissue chromophore whose light absorption properties depend on the oxygenation state of the tissue. In one embodiment, the tissue chromophore is related to $StO_2$. The initial measurement is taken in an unrestricted state in which the restriction means 12 does not restrict blood flow to the selected region.

After the initial measurement has been taken, the restriction means 12 is operated to restrict blood flow to the tissue region where the initial measurement was taken for a first predetermined period. Doing so reduces the amount of flowing oxygenated blood available to the tissue of the tissue region, causing an artificially induced or controlled ischemia in the localized tissue of the affected tissue region. The sensor 14 continues to collect data related to the tissue chromophore throughout the initial and restricted first predetermined period.

At the conclusion of the first predetermined period, blood flow to the selected tissue region is un-restricted or permitted. Uncertainty in the timing of the first predetermined period may be reduced by employing an automated activation and release of the restriction means 12 rather than relying on manual operation of the restriction means 12. The sensor 14 continues to collect data on the tissue chromophore following un-restriction of the blood flow. The tissue chromophore may continue to be measured for a predetermined period, or may simply be measured continuously for extended periods of time.

The length of the first predetermined period is based on several factors. First, the length of the first predetermined period should be sufficient to significantly reduce blood flow to the tissue region so as to permit calculation of a rate of change, or slope, of the measured tissue chromophore during the controlled ischemic event. However, pressure exerted by the restriction means 12 may be uncomfortable for the patient. Typically, then, the first predetermined period of restricted blood flow will last from about 30 seconds to about 5 minutes.

In other embodiments, rather than being based on a constant or predetermined time period, the first predetermined period may be based upon the measured tissue chromophore value. For example, blood flow may be restricted until a measured tissue chromophore value, such as $StO_2$, reaches a predetermined threshold value or a predetermined steady state value. In one embodiment, blood flow is restricted until the patient's measured $StO_2$ reaches 40 units. In still other embodiments, blood flow may be restricted until a predetermined minimum or threshold rate of change in the measured tissue chromophore over time is achieved. Following operation of the restriction means 12, the patient's tissue chromophore of interest, for example, $StO_2$, is sampled. Once the slope or rate of change between the most recent at least three to five samples reaches a minimum or threshold value, it can be assumed that the blood flow to the tissue region has been significantly reduced so as to permit calculation of a rate of change of the measured tissue chromophore throughout the duration of the controlled ischemic event.

In still other embodiments, the first predetermined period may be based on the temperature of the selected tissue region. It is known that reduced blood flow will result in reduced tissue temperature. Thus, the temperature of the selected tissue region may be monitored and blood flow restricted until the temperature of the selected tissue region reaches a predetermined threshold value.

Figure 2:
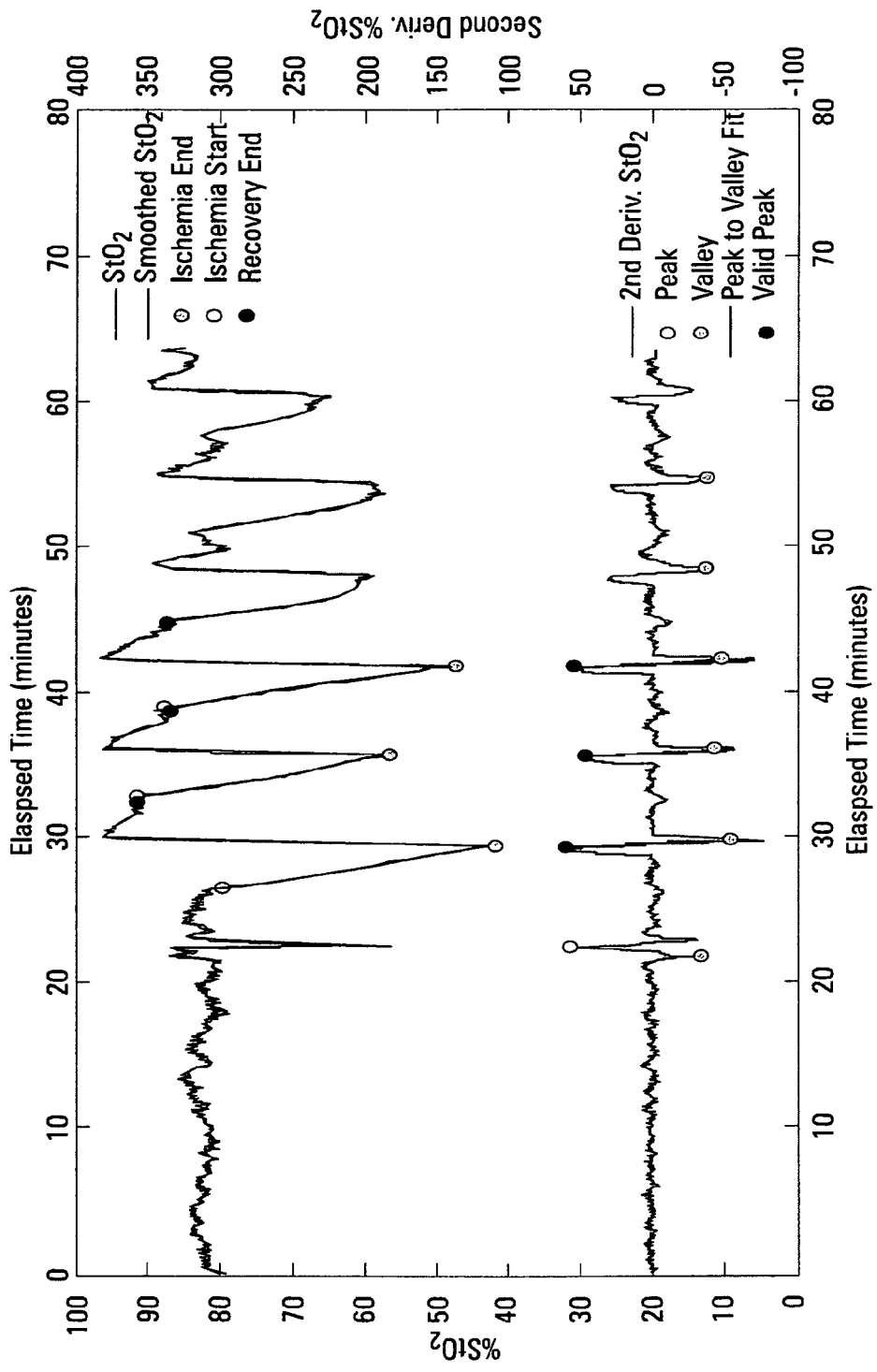
FIG. 2 is a graph illustrating ischemia start, ischemia end, and recovery endpoint detection examples as percent $StO_2$ versus time.

The upper waveform of FIG. 2 is a graph showing an exemplary waveform representing measurements of a tissue chromophore during the initial period, the first predetermined period in which blood flow is restricted, and a second period in which blood flow is un-restricted for a plurality of controlled ischemic events. The initial approximately 45 minutes of measurements represent restriction of arterial blood flow, while the remaining measurements represent restriction of venous blood flow. Using the data collected during the measurements, characterizing data related to the measured tissue chromophore may be automatically determined. Examples of such characterizing data include a slope of ischemia onset, a slope of ischemia recovery, an ischemia onset response time, an ischemia recovery response time and a hyperemia effect, all of which may also be adjusted for the total amount of hemoglobin present in the tissue.

In one embodiment, a start point to the controlled ischemic event, an "ischemia start point", and an end point to the controlled ischemic event, an "ischemia end point", may be determined. The ischemia start point and ischemia end point may be employed in determining characterizing data.

Determining an ischemia end point may be accomplished by first smoothing the measurement data. The data may be smoothed by running a second order polynomial fit of a number of consecutive tissue chromophore measurements, as is shown in the upper waveform of FIG. 2. A generally reliable fit may be obtained by running from five to twelve consecutive tissue chromophore measurements. In one embodiment, the data is smoothed by running a second order polynomial fit on eight consecutive tissue chromophore measurements. Then, the predicted tissue chromophore amount for the time point representing a tissue chromophore measurement behind the leading or most current tissue chromophore measurement is returned. In one embodiment, the tissue chromophore amount for the time point representing the third tissue chromophore measurement behind the leading tissue chromophore measurement is returned.

The smoothed data is then transformed into second derivative points of the tissue chromophore measurement, as is shown in the lower waveform of FIG. 2. In one embodiment, a fixed gap of ten consecutive measurements is used to calculate second derivative tissue chromophore amounts. In other embodiments, a second derivative of the polynomial equation used to smooth the data is used to transform the data.

Next, peaks of the second derivative points are identified. The peaks may be identified as second derivative points that exceed an average of local second derivative points by a first predetermined amount. In one embodiment, the peaks are identified if they are greater than the average of all second derivative points plus three standard deviations of all second derivative points. Instead, or in addition, a peak may be identified as a local maximum within the time interval representing ten tissue chromophore measurements leading and trailing the current second derivative tissue chromophore amount.

Next, valleys of the second derivative points are identified. Valleys are identified by identifying second derivative points that are less than an average of local second derivative points by a second predetermined amount. In one embodiment, a valley is identified if it is less than the average of all second derivative points minus 2.5 standard deviations of second derivative points. Instead, or in addition, a valley may be identified as a local minimum within the time interval representing ten tissue chromophore measurements leading and trailing the current second derivative tissue chromophore amount.

Next, valid peaks are identified. Valid peaks are those peaks that precede valleys within a predetermined time interval. More specifically, when restricting both arterial and venous blood flow, valid peaks are those relating to arterial blood flow rather than venous blood flow. In one embodiment, valid peaks are those peaks that precede a valley second derivative point within a predetermined time interval of about ⅔ of the controlled ischemia time (i.e., the first predetermined period of restriction). If multiple controlled ischemic events are replicated, valid peak second derivative points will also proceed or precede other valid peak second derivative points with a time separation greater than ⅔ of the controlled ischemia time (i.e., the absolute value of the time difference between adjacent valid peak second derivative peaks will be greater than ⅔ of the controlled ischemia time).

Next, a curve fitting on the second derivative points between each valid peak and its related valley is generated. This produces a correlation coefficient versus the actual second derivative data. In one embodiment, a linear curve is generated by performing a linear regression of the time series second derivative tissue chromophore amount in the time interval between a valid second derivative peak and the second derivative valley identified from the predetermined separation times. The correlation coefficient of the predicted versus actual second derivative tissue chromophore amounts evaluated from the linear regression model is returned.

Finally, the correlation coefficient is compared to a predetermined threshold value indicating a representative degree of fit. If a first predetermined relationship exists between the correlation coefficient and the predetermined threshold value, it is determined that the valley represents an ischemia end point. If the first predetermined relationship does not exist, then it is determined that the valley does not represent the ischemia end point. In one embodiment, the predetermined relationship is defined as a correlation coefficient less than approximately −0.90, indicating that a line of negative slope fits the valid second derivative peak and proceeding valley. This indicates that the current valid second derivative peak represents the ischemia end point.

In one embodiment, determining the ischemia start point includes identifying a data point or tissue chromophore amount that precedes the ischemia end point by the first predetermined period (a time interval equal to the controlled ischemia time). In other embodiments, the ischemia start point may be automatically determined as occurring upon activation of the restriction means 12 or when the restriction means 12 is operated to restrict blood flow. For example, the ischemia start point may be considered as occurring at the time of the beginning of the first predetermined period, or after a fixed interval following the beginning of the first predetermined period.

In one embodiment, determining characterizing data related to tissue oxygenation includes calculating an ischemia onset slope, or a rate of change of the measured tissue chromophore following the ischemia start point. A patient's ischemia onset slope is indicative of the rate at which oxygen is consumed in the measured tissue region.

Figure 3:
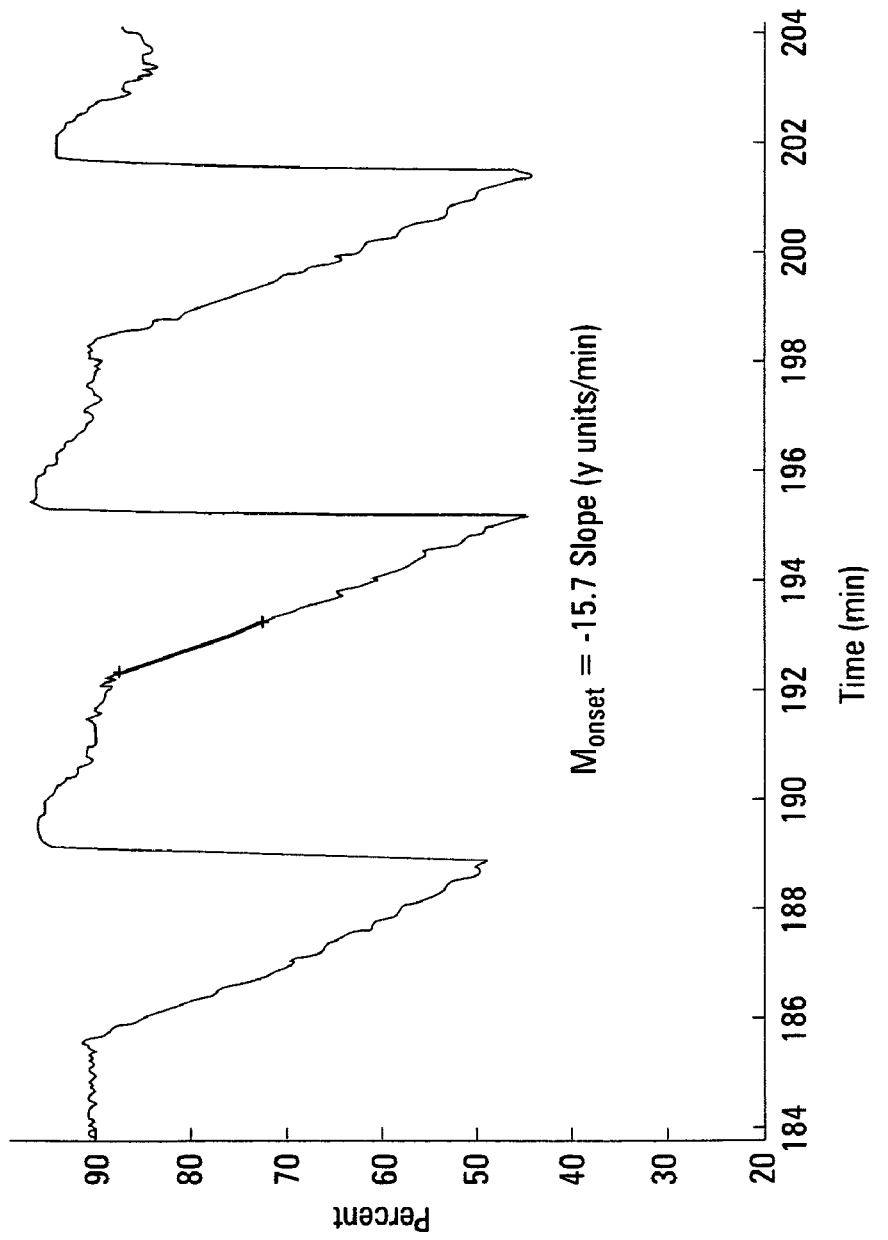
FIG. 3 is a graph illustrating an ischemia onset slope determination example as percent $StO_2$ versus time.

In one embodiment, calculating an ischemia onset slope, known as $M_{onset}$, as shown in FIG. 3, includes selecting data points that occur in a second predetermined period after the ischemia start point. The second predetermined time period should be less than the first predetermined period. In one embodiment, the second predetermined period may be approximately 1 minute. A curve fitting on the selected data points is then generated. The curve may be generated as a first order linear regression of the selected data points, where the tissue chromophore amount equals $M_{onset}$(time)+offset, using time or a measurement number as the independent variable. A correlation coefficient representative of the ischemia onset slope may then be generated.

Figure 4:
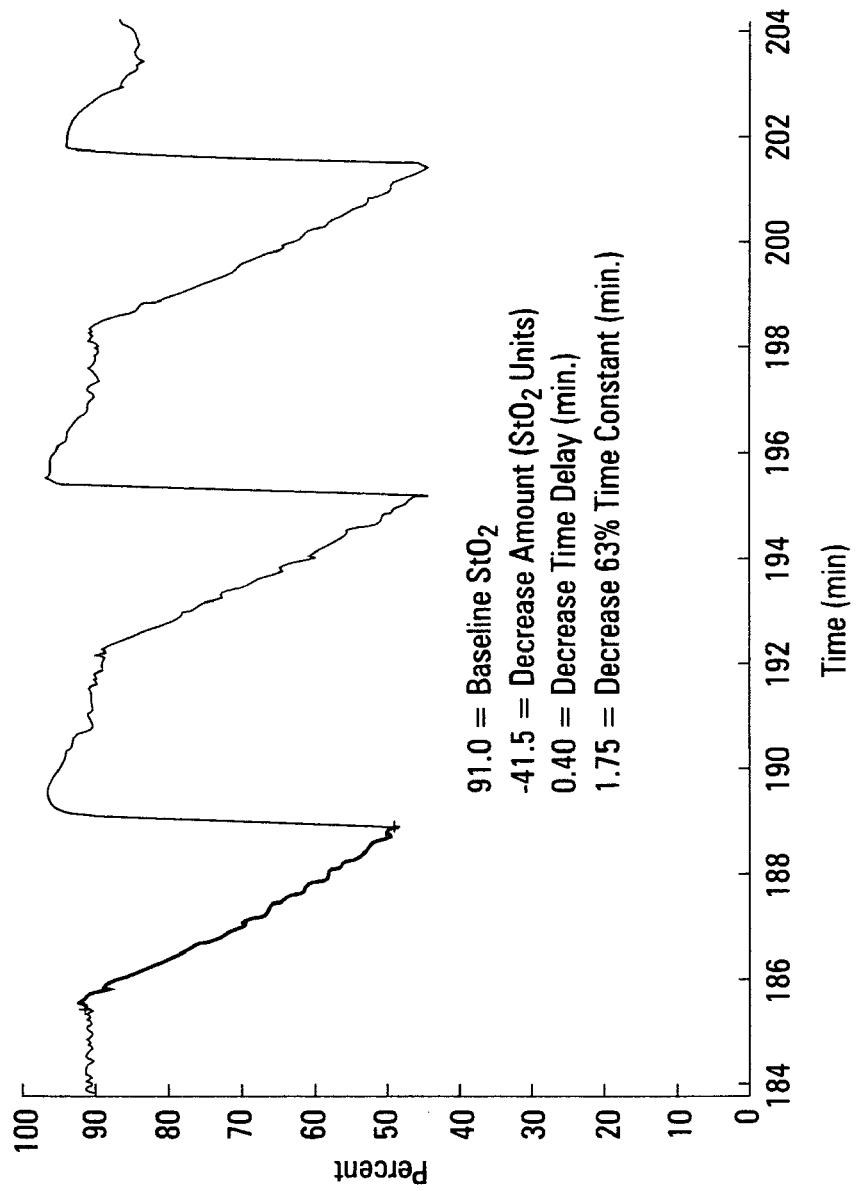
FIG. 4 is a graph illustrating an ischemia onset response time determination example as percent $StO_2$ versus time.

In another embodiment, as shown in FIG. 4, determining characterizing data related to tissue oxygenation further includes determining an ischemia onset response time. A patient's ischemia onset response time is the amount of time it takes for the patient's measured tissue chromophore to drop from a baseline level to a minimum level, and is indicative of the patient's oxygen consumption, utilization and/or uptake capabilities.

For a time interval beginning at the ischemia start point and ending at the ischemia end point, the data points are fitted to a non-linear exponential response curve. The response curve may have the equation:

$$CA_{fit} = \left(a_1 + b_1 * \left\{1 - \exp\left[\frac{(-\text{time} + b_2)}{b_3}\right]\right\}\right)$$

where $CA_{fit}$=fitted data points,
$a_1$=baseline data point value just before the start of ischemia,
$b_1$=minimum data point value occurring between the ischemia start point and the ischemia end point minus $a_1$,
$b_2$=the time delay between the ischemia start point and when the data points in the time interval begin a significant decrease, typically approximately 5% change, and
$b_3$=0.633, a time constant representing the time it takes for the tissue chromophore to change 63.3% of its absolute maximum change.

The ischemia onset response time is the time between $(a_1)$ and $(a_1+EQ[\text{minimum}(CA_{fit})-a_1])$ with EQ representing a fraction equilibrium time, a number between 0 and 1. For an EQ of approximately 0.95, the resultant ischemia onset response time is the 95% equilibrium response time for the tissue chromophore amount to reach its ischemia minimum or nadir point.

In one embodiment, determining characterizing data related to tissue oxygenation includes determining an end point to recovery from the controlled ischemic event after blood flow is un-restricted, a "recovery end point" and a maximum tissue chromophore amount after blood flow is un-restricted, a "recovery maximum point". The recovery end point and the recovery maximum point may be employed in determining flow-related characterizing data.

In one embodiment, the recovery maximum point is identified as the maximum tissue chromophore amount following the ischemia endpoint. The recovery maximum point may represent the end point of recovery analysis.

In one embodiment, the recovery end point is defined as the minimum data point occurring after the recovery maximum point. In other embodiments, the recovery end point is defined as the steady state value of the smoothed tissue chromophore measurement data following the ischemia endpoint. In one embodiment, the recovery end point occurs after the end of the first predetermined period and prior to the next consecutive controlled ischemic event.

In one embodiment, determining characterizing data related to tissue oxygenation includes calculating an ischemia recovery slope, or a rate of change of the tissue chromophore following the ischemia end point. A patient's ischemia recovery slope is indicative of the patient's oxygen delivery capabilities.

Figure 5:
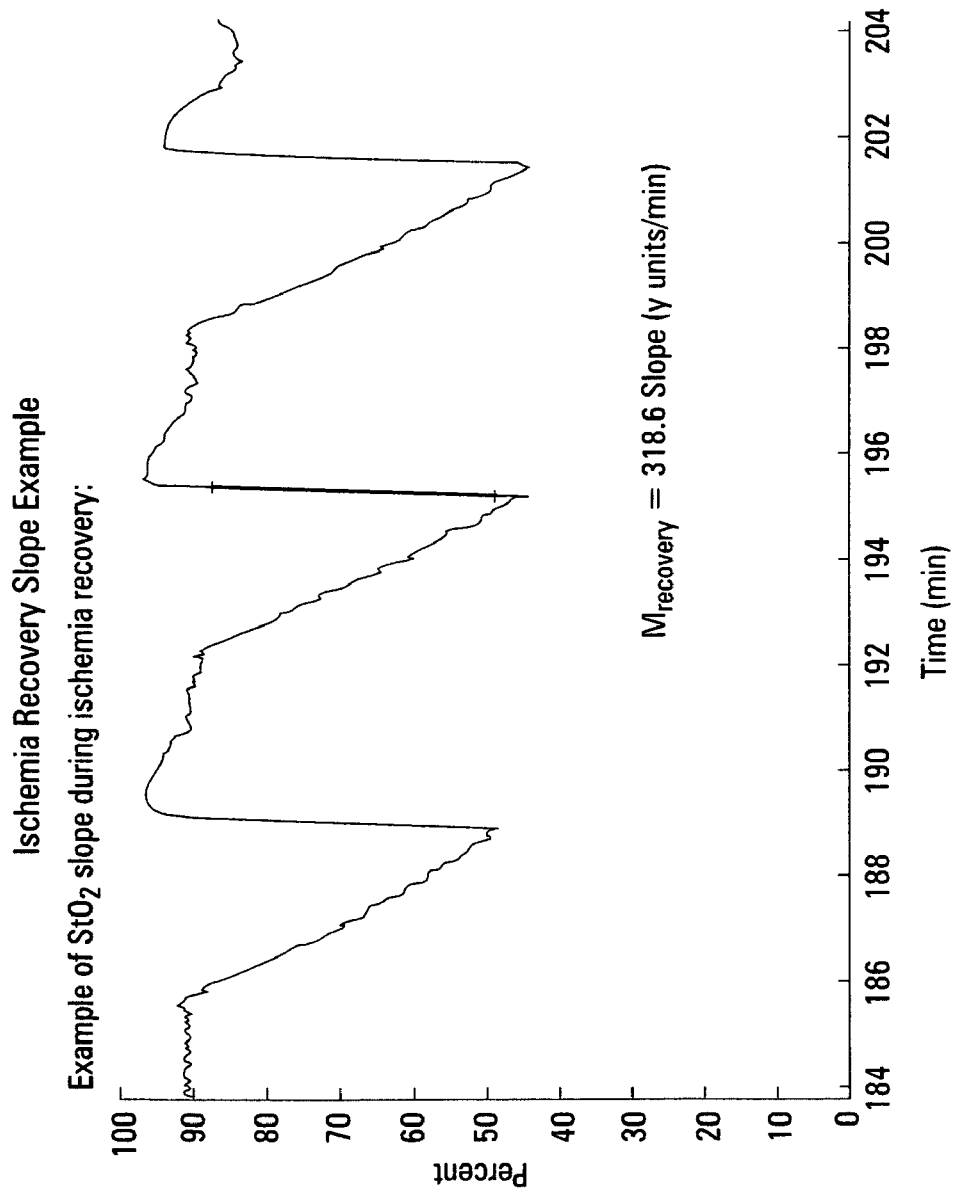
FIG. 5 is a graph illustrating an ischemia recovery slope determination example as percent $StO_2$ versus time.

In one embodiment, calculating the ischemia recovery slope $M_{recovery}$, as shown in FIG. 5, includes selecting data points occurring between the ischemia end point and the recovery end point or maximum point. A curve fitting on the selected data points is then generated. The curve may be generated as a first order linear regression equation where the tissue chromophore amount equals $M_{recovery}$(time)+offset, where time or a measurement number is used as the independent variable. A correlation coefficient representative of the ischemia recovery slope may then be generated. In another embodiment, the data points are selected as occurring in a second predetermined period after the ischemia start point.

Figure 6:
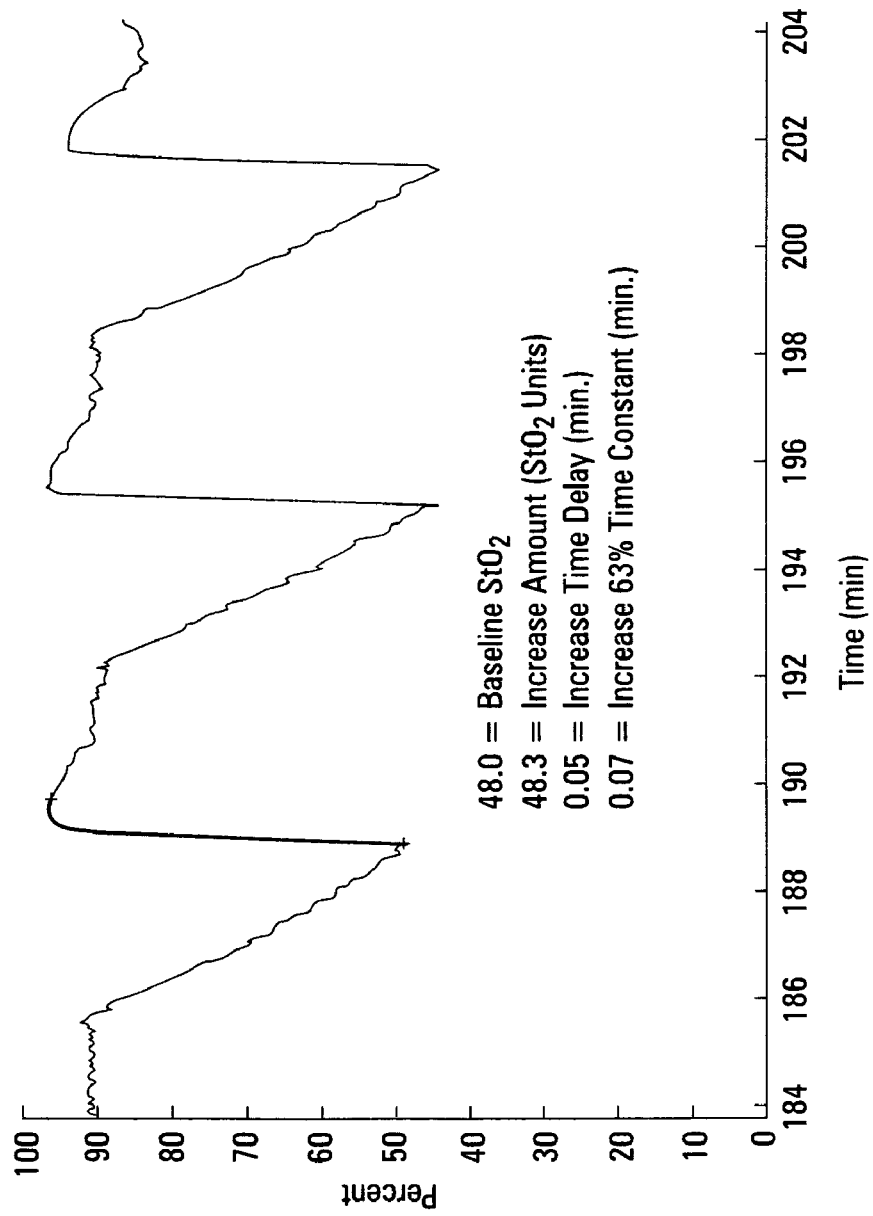
FIG. 6 is a graph illustrating an ischemia recovery time determination example as percent $StO_2$ versus time.

In another embodiment, as shown in FIG. 6, determining characterizing data related to tissue oxygenation further includes determining an ischemia recovery response time. A patient's ischemia recovery response time is the amount of time it takes for the measured tissue chromophore to go from a minimum level just prior to the ischemia end point to a maximum level upon release of the restriction means 12. The ischemia recovery response time is indicative of the patient's oxygen delivery capabilities, such as flow rate of hemoglobin within the tissue.

For a time interval beginning at the ischemia end point and ending at the recovery maximum point, the data points are fitted to a non-linear exponential response curve. The response curve may have the equation:

$$CA_{fit} = \left(a_1 + c_1 * \left\{1 - \exp\left[\frac{(-\text{time} + c_2)}{c_3}\right]\right\}\right)$$

where $CA_{fit}$=fitted data points,
$a_1$=baseline data point just before the start of ischemia,
$c_1$=maximum tissue chromophore value occurring between the ischemia endpoint and the recovery maximum point minus $a_1$,
$c_2$=a time delay between the start of ischemia and when the data points in the time interval begin a significant increase, typically approximately a 5% increase, and
$c_3$ is 0.633, a time constant representing the time it takes for the tissue chromophore to change 63.3% of its absolute maximum change.

The ischemia recovery response time is the time between $(a_1)$ and $(a_1+EQ[\text{maximum}(CA_{fit})-a_1])$ is determined, with EQ representing a fraction equilibrium time, a number between 0 and 1. For an EQ of about 0.95, the resultant ischemia recovery response time is the 95% equilibrium response time for the tissue chromophore amount to reach its recovery maximum point which is representative of an ischemia recovery time.

In another embodiment, determining characterizing data related to a tissue oxygenation includes adjusting the measured tissue chromophore data or characterizing data to reflect the total amount of hemoglobin present in the tissue. The total amount of hemoglobin present in the tissue can affect the rate of hemoglobin desaturation, i.e., the ischemia onset slope or the ischemia onset response time, as well as the rate of hemoglobin saturation, i.e., the ischemia recovery slope or the ischemia recovery time.

In one embodiment, the total amount of hemoglobin in the tissue may be calculated using the process described in U.S. Pat. No. 6,473,632 titled TOTAL HEMOGLOBIN CONCENTRATION MEASUREMENT, the entire disclosure of which is hereby incorporated herein by reference.

By using the combination of both a single term ratio of a second derivative light absorbance value of the tissue and a single term non-ratioed second derivative light absorbance value of the tissue, a measure of the volume percentage of a tissue chromophore whose light absorption properties depend on the oxygenation state of the tissue, such as hemoglobin (a value that directly correlates with hemoglobin concentration), can be calculated.

In one configuration the wavelength gap used to calculate the second derivative values (i.e., the interval between adjacent absorbance wavelengths used in the second derivative calculation) is 40 nm. At this gap size only four wavelengths are used to calculate both the percentage of oxidized hemoglobin and the total amount of hemoglobin in the tissue. The forward calculated second derivative absorbance peak at 720 nm (corresponding to the deoxyhemoglobin absorption band of 760 nm) is used to empirically derive the relationship between the total amount of hemoglobin in the tissue and the second derivative absorbance. Second derivative gap sizes other than 40 nm can also be used to derive the hematocrit algorithm. Also, other wavelength regions (e.g., visible or infrared) corresponding to other oxyhemoglobin or deoxyhemoglobin absorbance maximums could be used.

The tissue chromophore measurements made in accordance with the algorithms described herein can be used by an instrument in connection with tissue recognition algorithms. Inaccurate and/or invalid measurements of % $StO_2$ or other measured parameters can be displayed by the display 18 if the sensor 14 is not properly located on the tissue to be measured. The tissue chromophore can be used by the instrument to determine whether the sensor 14 is properly positioned and the measurement is accurate. For example, in connection with some or all of the tissue chromophore measurements, the control module 16 can compute the total amount of hemoglobin in the tissue using the algorithm described herein, and display the measurement as an accurate measurement only if the measurement is representative of a predetermined minimum level. If the total amount of hemoglobin in the tissue is below the predetermined level, the display 18 can generate a display indicating that the sensor 14 is not properly positioned.

Total hemoglobin measurements can be generated as a function of current second derivative spectroscopy values and stored data describing the relationship between the second derivative values and the tissue hemoglobin concentration. In the embodiment described below, the stored relationship data is data describing a set of lines or slopes (or curves if preferred), each of which is associated with a constant oxidation state of hemoglobin.

The proper stored relationship data can be selected by the control module 16 on the basis of the measured hemoglobin oxidation state. From this data and the current second derivative spectroscopy value, the total amount of hemoglobin in the tissue can be computed by the control module 16.

At multiple levels of hematocrit (HCT), the second derivative spectral features of the blood are recorded at a predetermined (e.g., 5 mm) probe spacing over multiple % $StO_2$ values within the 0%-100% range. For each hematocrit the 720 nm second derivative peak is fitted to a linear equation.

At each constant level of % $StO_2$, the second derivative 720 nm feature is related to % hematocrit with extrapolation to 0% hematocrit. There is a linear relationship between the 720 nm second derivative and hematocrit at hematocrits of about 25% and less.

Using linear extrapolation to 0% hematocrit and empirical measurements at 25% and 15% hematocrit, a lookup table of relationship data which describes the sensitivity of hematocrit to the 720 nm second derivative values (lines of constant % $StO_2$) can be created. The slopes are functionally related to the ratio of the second derivative at 680 nm to the second derivative at 720 nm.

The stored relationship data described above is subsequently used during tissue hemoglobin concentration measurements. Upon measuring % $StO_2$ (e.g., using conventional algorithms and scaled second derivative values at 680 nm) the corresponding slope value (Mso2 or HCT slope) is found within the lookup table. The predicted hematocrit value is then:

$$\% HCT = (Mso2) \times (D720/PSF)$$

where D720 is the forward calculated second derivative at 720 nm using the 40 nm gap PSF is the relative path length change due to probe spacing.

The concentration of tissue hematocrit is generally less than 25%, and is usually in the 1%-10% range. When evaluating probe position on the basis of hemoglobin concentration measurements, relatively high measurement accuracy near the lower end of the range is sufficient. For example, the threshold for determining whether the probe is on or off tissue can be in the range of 1% measured hemoglobin concentration. The linear range of spectral features versus hematocrit concentration need only be used for this application. However, in accordance with the present invention, the measurement accuracy can be extended to greater percentages of hematocrit by redefining the algorithm to account for nonlinearities. The algorithm could, for example, be redefined as a multiple regression algorithm consisting of multiple slope and second derivative transformations (linear transformations). Examples of nonlinear equations include:

$$\% HCT = (Mso2_1) \times (D720/PSF) + (Mso2_2) \times \mathrm{Log}(D720/PSF),$$

or $$\% HCT = (Mso2_1) \times (D720/PSF) + (Mso2_2) \times (D720/PSF)^{1/2} + (Mso2_3) \times (D720/PSF)^{1/3} + \ldots$$

where $Mso2_1$, $Mso2_2$, ... are nonlinear slope value coefficients which can be stored in the lookup table.

The probe (sensor) scaling factor (PSF) can be empirically determined by collecting second derivative spectral measurements of a chromophore medium, preferably having constant scattering and absorption properties, with optical probes having variable distances between the optical send and receive fibers. The spectral measurements at each probe spacing are then referenced (ratioed) to one of the fixed probe spacing spectral measurements at a particular wavelength of interest. The ratio of one second derivative spectrum value at a probe spacing of interest to the second derivative spectrum value of the reference probe spacing then reflects the probe scaling factor. The probe scaling factor can be determined at calibration stored in memory.

Figure 7B:
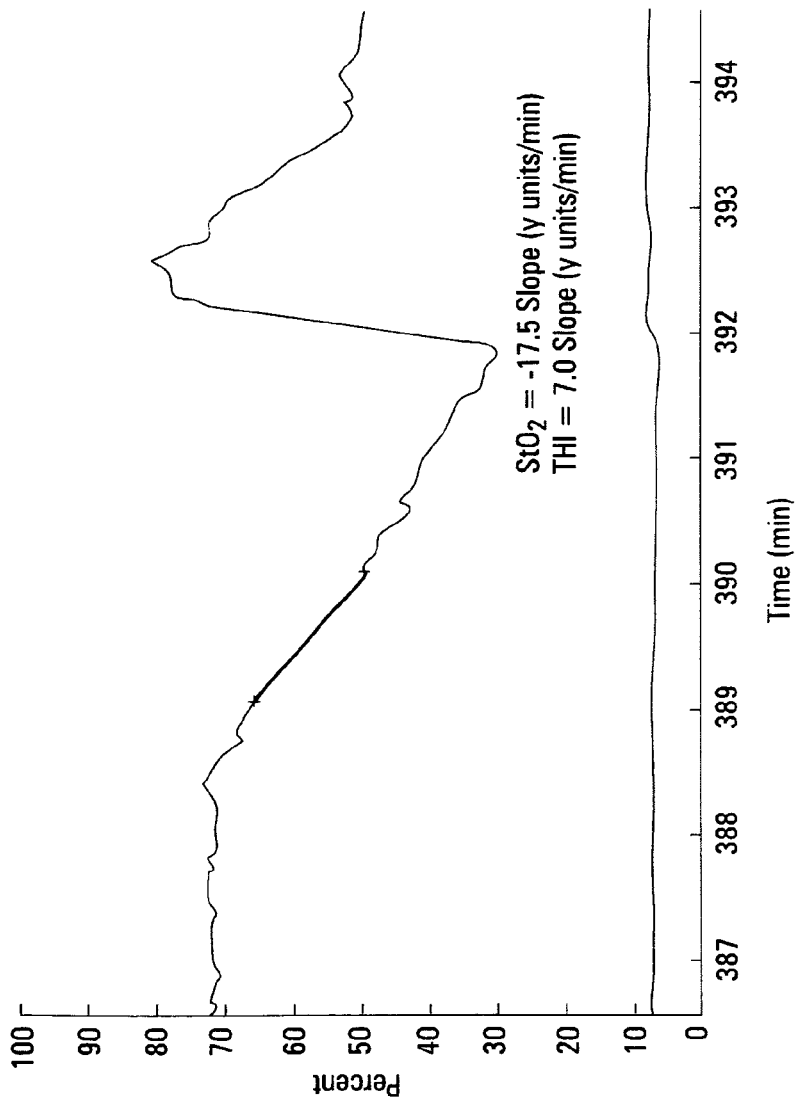
FIG. 7B is a graph illustrating an ischemia onset slope determination example as percent $StO_2$ versus time in which the patient has a low volume of hemoglobin in the tissue.
Figure 7C:
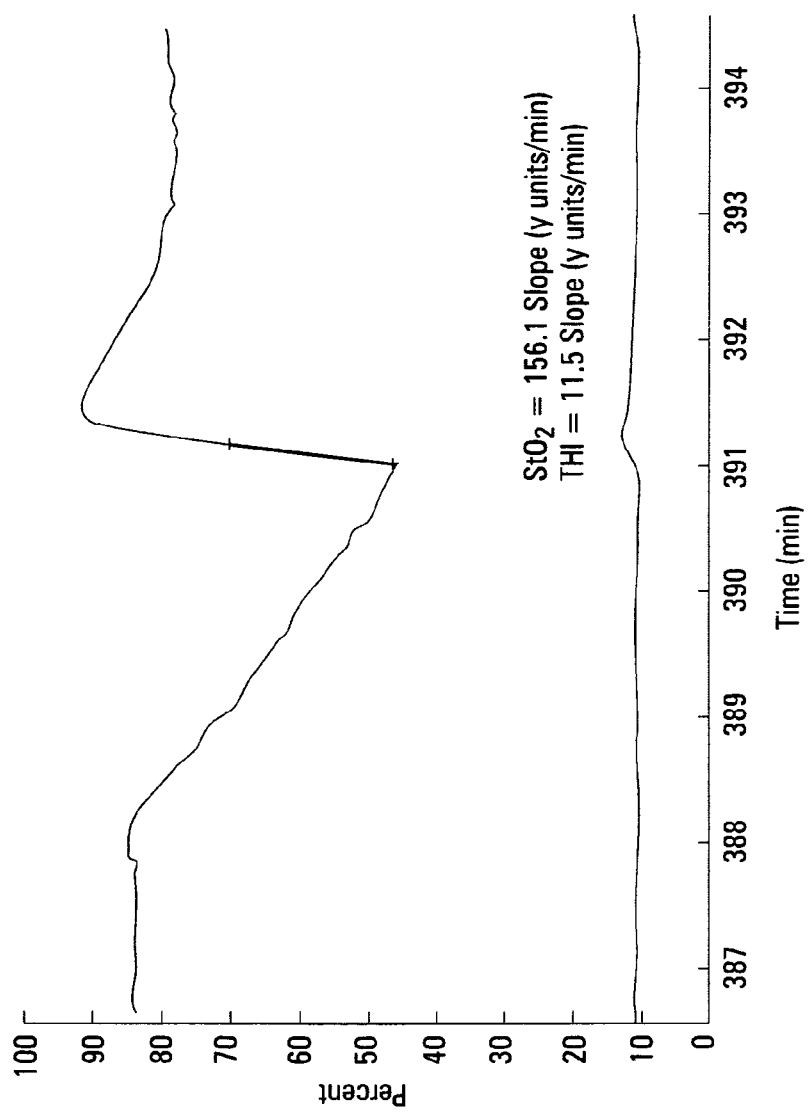
FIG. 7C is a graph illustrating an ischemia recovery slope determination example as percent $StO_2$ versus time in which the patient has a high volume of hemoglobin in the tissue.
Figure 7D:
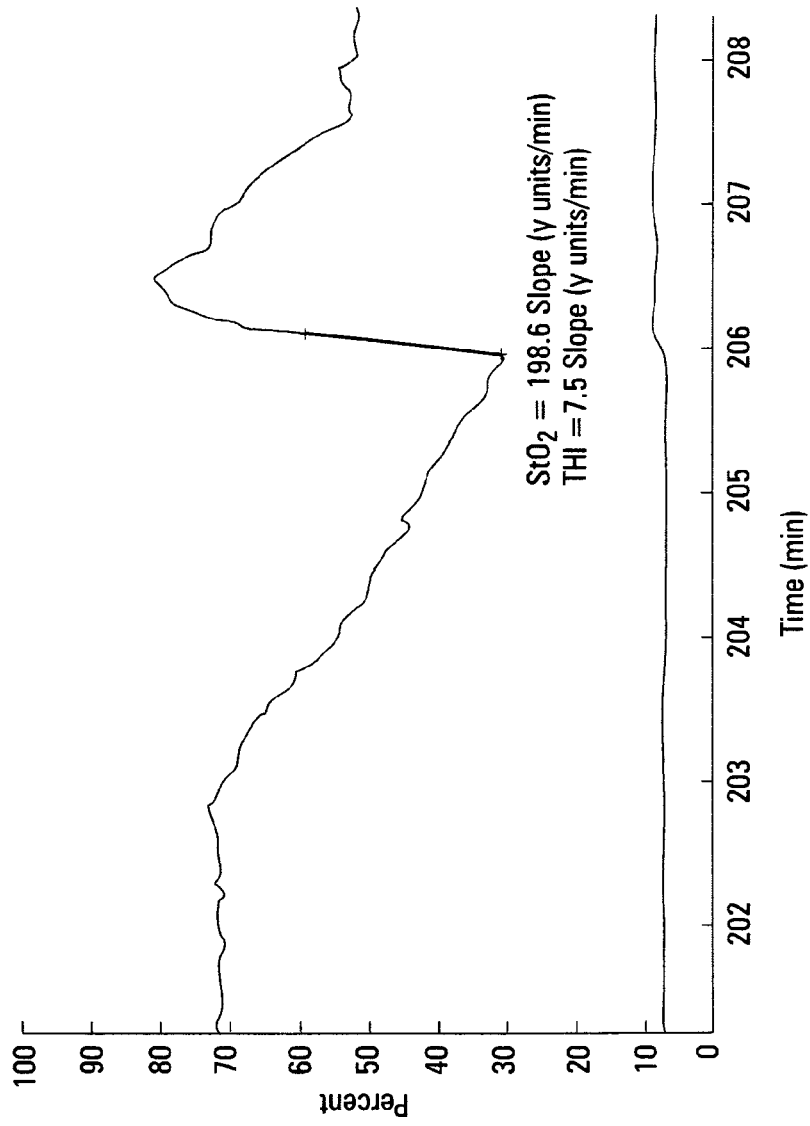
FIG. 7D is a graph illustrating an ischemia recovery slope determination example as percent $StO_2$ versus time in which the patient has a low volume of hemoglobin in the tissue.

FIG. 7A is a graph illustrating the ischemia onset slope of a patient having a relatively high volume of the hemoglobin in the tissue. In contrast, FIG. 7B is a graph illustrating is the ischemia onset slope of a patient having a relatively low volume of hemoglobin in the tissue. FIGS. 7C and 7D show the ischemia recovery slope of a patient having relative high and low volumes of hemoglobin in the tissue. Thus, adjusting the measured tissue chromophore data or characterizing data to reflect the total volume of hemoglobin in the patient's tissue can provide characterizing data on absolute oxyhemoglobin concentration, which may be more representative of actual oxygen consumption and flow.

In one embodiment, adjusting the measured tissue chromophore data to reflect the total amount of hemoglobin in the tissue includes multiplying the measured data by the average total amount of hemoglobin during the controlled ischemic event. The adjusted data is then used to determine adjusted characterizing data, such as ischemia onset slope and ischemia onset response time.

In another embodiment, determining characterizing data related to tissue oxygenation includes determining the patient's capacity to increase post-ischemia flow beyond the flow rate prior to ischemia. When blood flow is initially restricted, blood vessels tend to dilate in an attempt to increase flow. Thus, when flow is permitted after the first predetermined period, the vessels are dilated and exhibit a reduced vascular resistance than prior to the controlled ischemia event. The reduced vascular resistance means that the post-ischemia flow will be temporarily greater than prior to ischemia, an effect known as hyperemia. Quantification of this temporary hyperemia relates to the patient's ability to recover from an accumulated oxygen debt.

Figure 8:
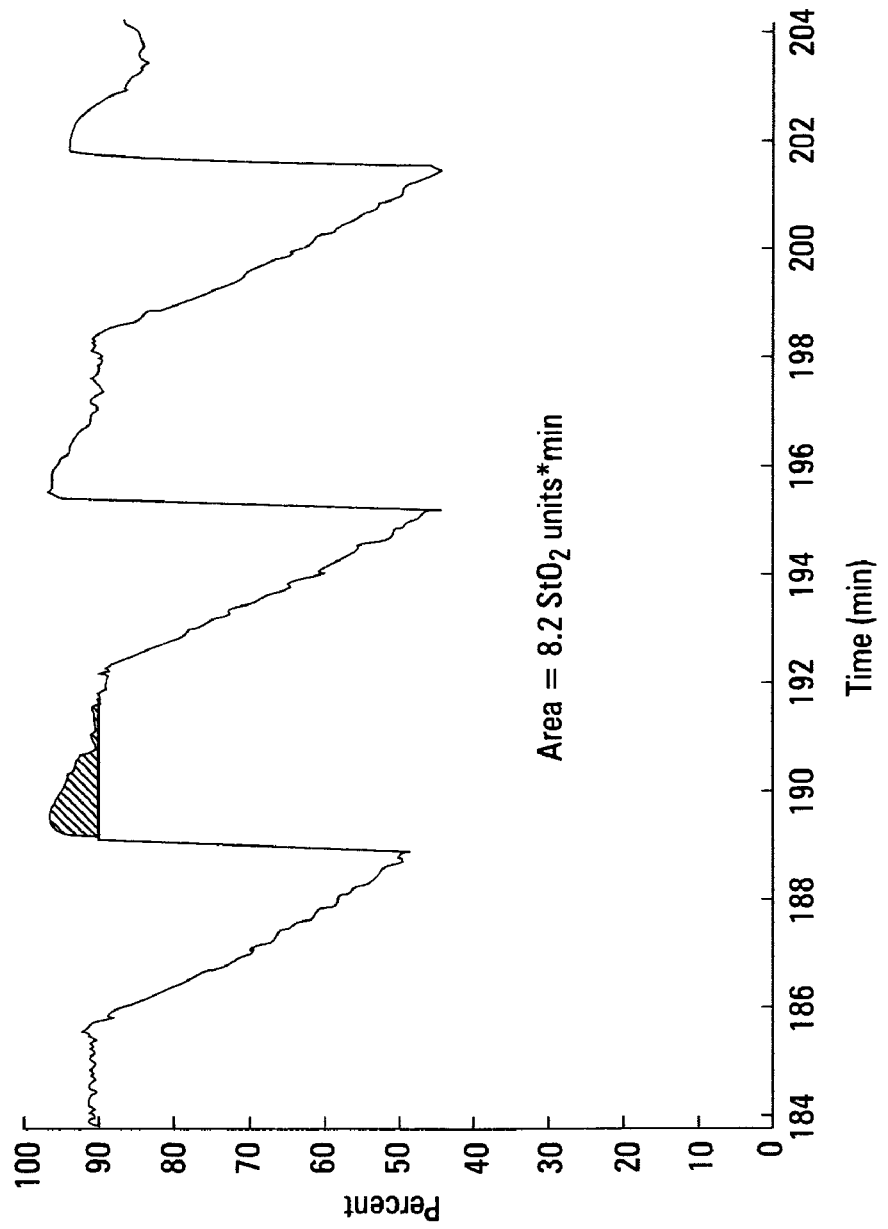
FIG. 8 is a graph illustrating a hyperemia effect as area under a patient ischemia recovery curve.

The hyperemia effect may be described in several ways. In one embodiment, shown in FIG. 8, the hyperemia effect is described as a recovery area, or the area beneath the ischemia recovery curve which is greater than the initial tissue chromophore measurement and occurs between the end of the first predetermined period and the recovery end point. Determining the recovery area includes identifying a minimum data point occurring between the recovery maximum point and the recovery end point. The data points occurring in a time interval between the ischemia end point and the recovery end point are integrated for data points greater than the minimum data point. The recovery area may be determined according to the equation:

$$\text{Recovery Area} = \sum_{t0}^{tf} (\Delta \text{time} * CA_{avg})$$

where $\Delta$time is the time interval between consecutive chromophore measurements, and $CA_{avg}$ is the average of two adjacent chromophore amount measurements.

In other embodiments, the hyperemia effect may be described as the maximum tissue chromophore amount following the ischemic event i.e., the recovery maximum point, the difference between the recovery maximum point and the initial tissue chromophore amount, or the difference between the recovery maximum point and the recovery end point.

System 10 may be employed to characterize tissue oxygenation data and to provide a characterization of the patient's current ischemic response as well as to provide real-time monitoring of the patient's dynamic response to ischemic events. Changes in "characteristics" or characterized measurement data representative of the patient's oxygen consumption, delivery and flow capabilities may be monitored as indicators of the patient's physiologic status and for determining trends in the patient's physiologic status.

The patient's ischemic response characteristics may be monitored upon, for example, intake into an emergency room. For example, the patient may be subjected to controlled ischemic events periodically over an extended period of time. An exemplary use would be for the patient to be subject to controlled ischemic events every five minutes for 24, 48 or 72 hours.

The equations described above may be used to generate characterizing data relating to oxygen consumption, oxygen delivery, etc., from the raw measurement data of any tissue chromophore whose light absorption properties depend on the oxygenation state of the tissue. For example, system 10 may be employed to characterize a patient's ischemic response based upon changes in oxyhemoglobin, deoxyhemoglobin and total amount of hemoglobin in the tissue.

Tissue chromophore measurement data and characterizing data or characteristics may be displayed on the display 18 in a variety of formats. In one embodiment, patient data is displayed on the display 18 in relation to corresponding data of a control population. For example, patient data may be displayed on the display 19 as a distribution meter plot, a distribution statistic trend plot or an analysis trend plot relative to the control population statistics. In the following figures, patient measurements and characterizing data are generally shown in terms of $StO_2$ data. However, as discussed previously, the methods and apparatus of the present invention may be used to monitor a patient's ischemic response based upon the measurement of any tissue chromophore whose light absorption properties depend on the oxygenation state of the tissue.

Figure 9:
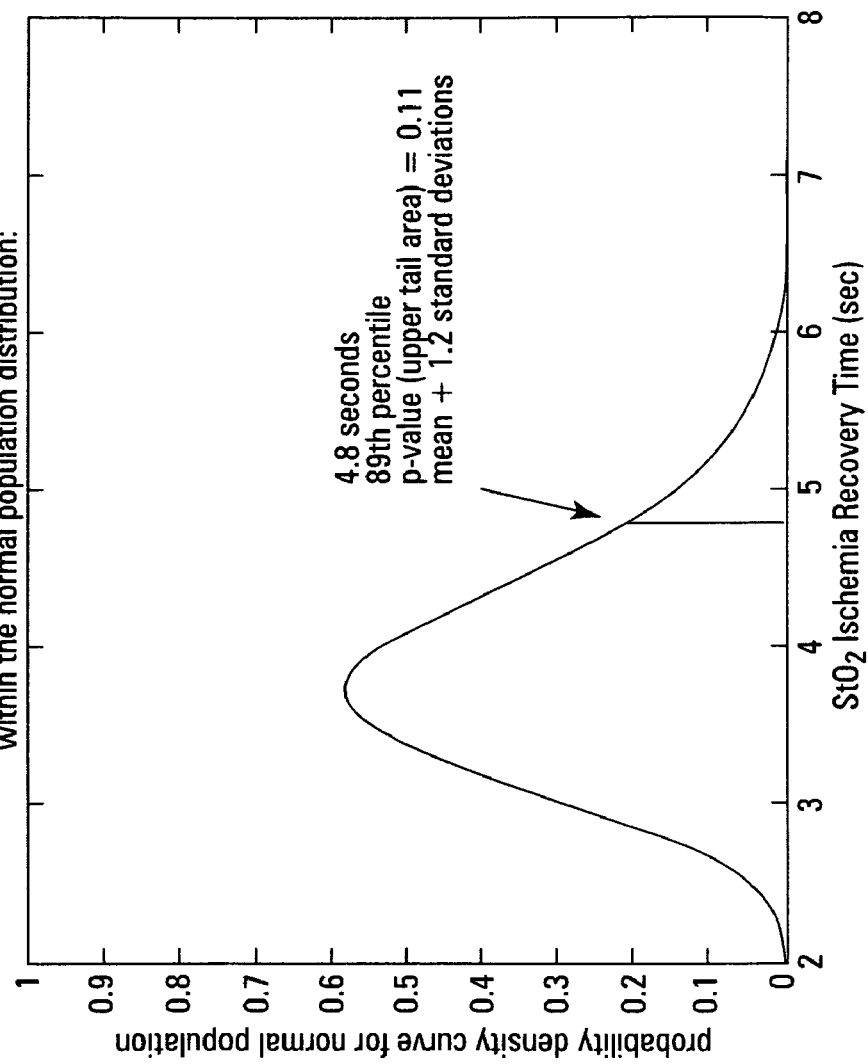
FIG. 9 is a graph illustrating a patient ischemia recovery time displayed relative to a control population as a distribution meter plot with the patient ischemia recovery time occurring within the control population distribution.
Figure 10:
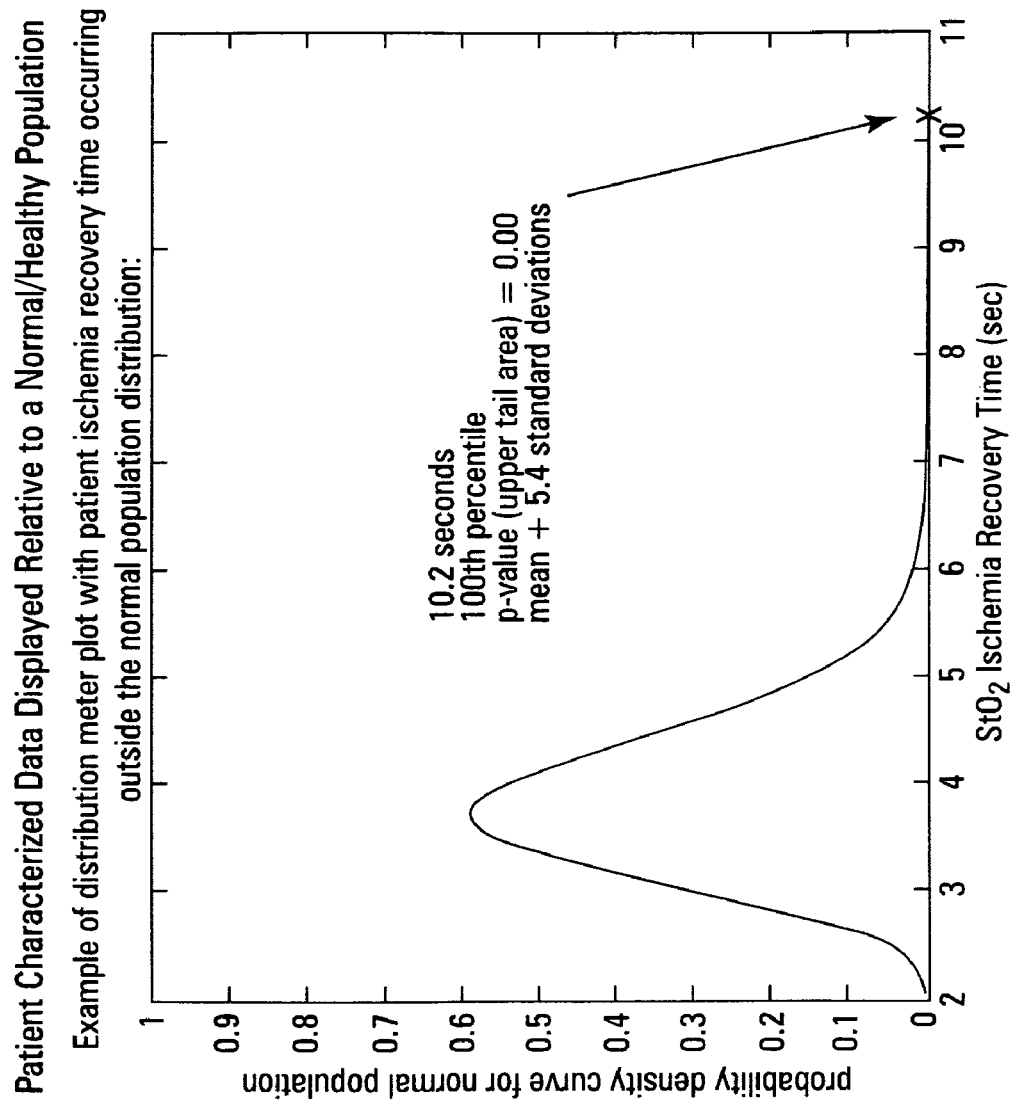
FIG. 10 is a graph illustrating a patient ischemia recovery time displayed relative to a control population as a distribution meter plot with the patient ischemia recovery time occurring outside the control population distribution.

FIG. 9 shows one embodiment of the display 18 format in which a distribution meter plot of measurements from a control population are pre-characterized and fit to a distribution curve. Such a distribution curve may be a log normal probability density function. As the patient is monitored, individual or mean tissue chromophore measurements are characterized and plotted on the distribution curve showing the patient characterized data relative to the distribution center and spread of the control population. Differences between the patient data and the control population data may be displayed in terms of mean or median and standard deviation or percentile. FIG. 9 shows an example of such a display in which the patient characterized measurement, ischemia recovery response time, occurs within the control population distribution. In contrast, FIG. 10 shows an example of a display in which the patient ischemia recovery response time occurs outside the control population distribution.

Figure 11:
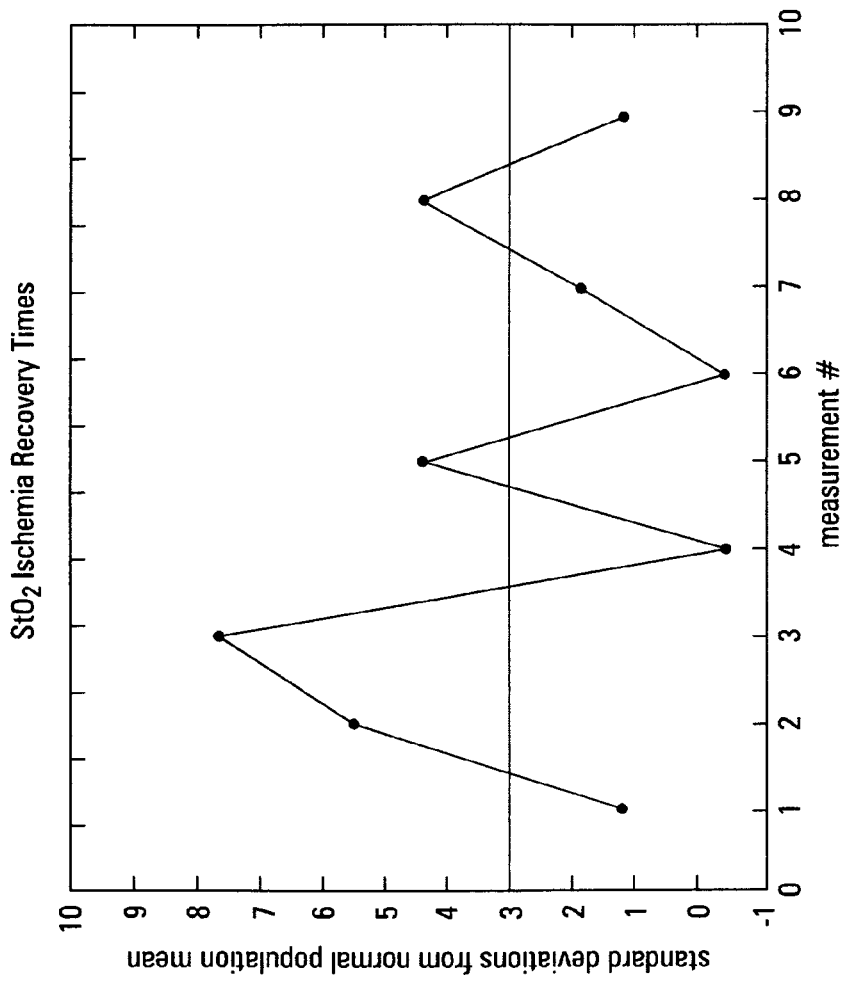
FIG. 11 is a graph illustrating a patient ischemia recovery time displayed relative to a control population as a distribution statistic trend plot for multiple ischemic events.

FIG. 11 shows another embodiment of the display 18 format in which a distribution statistic trend plot of repeated patient tissue chromophore normal distribution position measurements are characterized and scatter plotted or line graphed versus time. Examples of distribution position measurements showing the distance of an individual or mean patient characterized measurement relative to a control population distribution can include percentile, t, z or f value, p-value, curve area left or right of measurement, difference between patient characterized measurement and population mean, and standard deviation.

Figure 12:
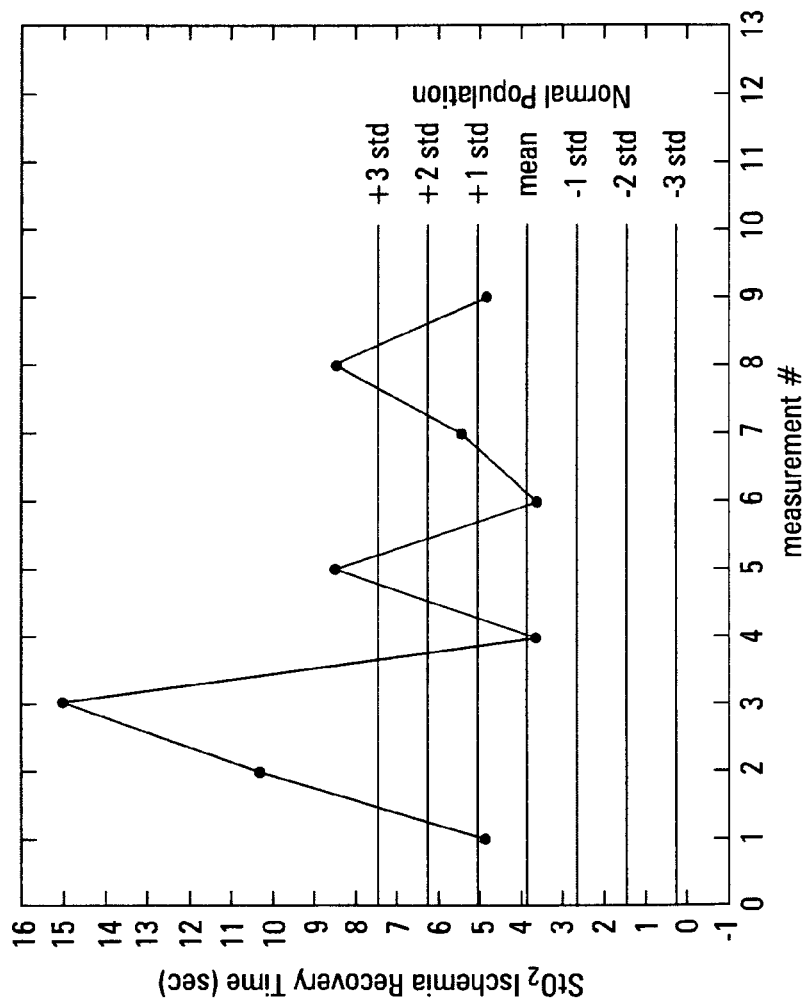
FIG. 12 is a graph illustrating a patient ischemia recovery time displayed relative to a control population as a tissue chromophore trend plot relative to control population statistics.

FIG. 12 shows another embodiment of the display 18 format in which repeated patient analysis trends are plotted relative to control population statistics. Patient individual or mean characterized tissue chromophore measurements are plotted on a scatter plot or a line graph versus time with control limits shown as constant lines representing the center and spread of a pre-characterized control population.

Figure 13:
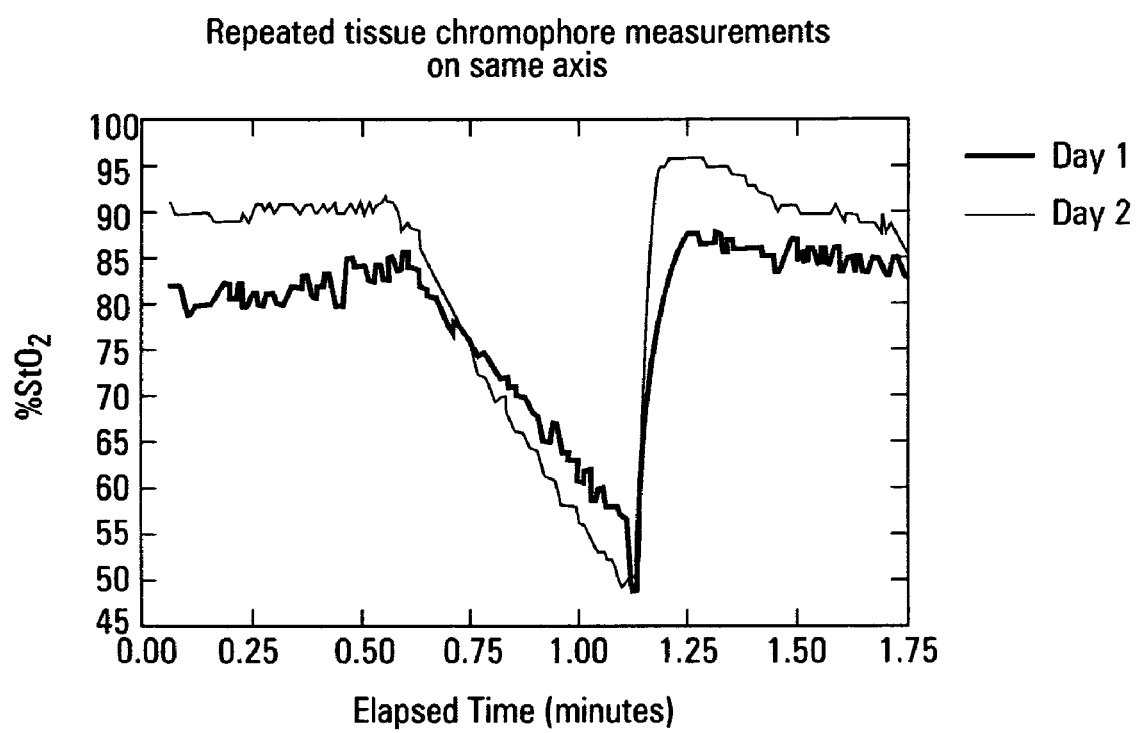
FIG. 13 is a graph illustrating patient tissue chromophore measurements for two controlled ischemic events as percent $StO_2$ versus time displayed on the same time axis.

In addition to displays for the purposes of comparison, as described above, the display 18 may also show the patient's tissue chromophore data for the current or most recent controlled ischemic event. In other embodiments, the display 18 may show the patient's averaged data over multiple ischemic events. FIG. 13 shows an embodiment of the display 18 format in which multiple tissue chromophore measurements are plotted over an extended period of time. By placing each measurement on the same X-Y axis, any trend or change in the patient's ischemic response over time can be conveyed. The display of FIG. 13 may be shown along with a control population comparison display as described above so as to provide the user with a more complete view of the patient's ischemic response characteristics.

The user, for example, the physician, may select from among various display formats the format which he/she believes conveys information in a useful manner. Alternately, the control module 16 may be adapted to automatically display a given tissue chromophore measurement or characterizing data in a display format pre-selected as conveying information in a standardized or more useful manner.

In one embodiment, the display 18 includes an alarm or other indicia for indicating when a measured tissue chromophore is outside of a pre-determined value or range of values. For example, the display 18 may provide an alarm when the patient's characterized data exceeds the $95^{th}$ percentile or drops below the $5^{th}$ percentile in relation to the control population. In other embodiments, the display 18 may provide an alarm when changes in the patient's characterized data are outside of a pre-determined value or range. The predetermined values may be set by the user, i.e., the physician, or may be programmed by the manufacturer. Furthermore, the system 10 may be provided with a plurality of predetermined values selectable by the user. The indicator or alarm may be a visual, auditory or sensory mechanism or other means for indicating an alarm status.

The above-described predetermined values, such as predetermined values relating to ischemia slope and recovery time, may be based upon corresponding tissue chromophore measurements of control populations. In one embodiment, the control population is known to be healthy or normal, in which case patient data is characterized and/or displayed in relation to the tissue oxygenation characteristics of a normal or healthy population. In other embodiments, the control population may be known to be abnormal or unhealthy, for example, having a known condition or disease. In this case, the patient data is characterized and/or displayed in relation to the tissue oxygenation characteristics of a known abnormal or unhealthy control population.

Patient data may also be characterized and displayed in relation to a control population populated with the data of individuals sharing a selected physical attribute with the patient, such as sex, weight range or age range. In other embodiments, a control population may be populated with the data of individuals sharing a selected health-related attribute with the patient, such as smoking vs. non-smoking. In this manner, differences between the tissue chromophore data of the control population and the patient due to the selected attribute may be reduced. This may provide a more accurate characterization of the patient's tissue oxygenation, and a more accurate display of the patient's characterizing data in relation to the data of the control population.

In one embodiment, the display 18 or control module 16 may be adapted to allow the user to select from among a plurality of control populations for use in characterization and display of the patient's data. In other embodiments, the display 18 or control module 16 may be adapted to prompt the user to enter data regarding a selected attribute(s) of the patient and for the control module 16 to automatically select a control population sharing the selected attribute(s).

The physician may use the information displayed on the display 18 to monitor and evaluate the patient's current ischemic response as well as the patient's dynamic ischemic response in real time over an extended period of time. For example, the patient's ischemic response may be monitored upon admission to an emergency room or intensive care unit, or when disorders such as shock are suspected. Furthermore, the patient's ischemic response may be monitored over the duration of a traumatic event or disease cycle to evaluate progression, recovery and response to medication or other therapy.

In another embodiment, system 10 provides a method of characterizing a patient's physiologic state based upon their ischemic response in relation to a control response of known population. In one embodiment, based upon comparison of the patient's characterizing data to a control population, the patient's ischemic response may be characterized as normal or abnormal. For example, a patient having characterizing data such as an ischemia onset slope or recovery slope above the $95^{th}$ percentile or below the $5^{th}$ percentile may be determined to have an abnormal ischemic response. In other embodiments, a determination of normal or abnormal may be made if the patient's characterizing data is more than two standard deviations from the control population. Limits of the normal and abnormal classifications may be pre-determined or may be set by the user. The limits may be determined in terms of percentile, t, z or f value, p-value, curve area left or right of measurement, difference between patient characterized measurement and population mean, and standard deviation. Furthermore, different classification limits may be applied to different types of characterizing data.

In another embodiment, system 10 provides a method of characterizing a patient' ischemic response as healthy or unhealthy based upon a comparison of the patient's ischemic response to the ischemic response of a control population. As described above, each of the types of characterizing data relates to a physiologic aspect of the ischemic response, for example, oxygen consumption and oxygen delivery. A patient having a characteristic such as ischemia onset slope above the $95^{th}$ percentile may be consuming oxygen more quickly than the control population because of an underlying physiologic or disease defect. Similarly, a patient having an ischemia onset slope below the $5^{th}$ percentile may be consuming oxygen more slowly than the control population because of an underlying physiologic or disease defect. Based upon a comparison of the patient's ischemic response to the control population, the patient's ischemic response may be determined to be healthy or unhealthy. Furthermore, as described above, a determination of whether the patient's ischemic response in relation to the control population may be a further indicator of the patient's health.

Limits of the healthy and unhealthy classifications may be pre-determined or may be set by the user. The limits may be determined in terms of percentile, t, z or f value, p-value, curve area left or right of measurement, difference between patient characterized measurement and population mean, and standard deviation. Furthermore, different classification limits may be applied to different types of characterizing data. Although similar limits have been described in relation to a determination of normal/abnormal and healthy/unhealthy, such limits need not be the same. For example, a patient characteristic such as ischemia onset slope may be determined to be abnormal, and thus worthy of continued monitoring, but not actually rise to the level of an unhealthy determination.

In another embodiment, system 10 provides a method of determining if a patient is becoming progressively healthier or closer to a normal state versus unhealthier or closer to an abnormal state. For example, a patient characteristic trending toward an abnormal or unhealthy state relative to a control population, as described above, may be determined as progressing towards an unhealthy physiologic state. Conversely, a patient whose characteristic data is trending toward a normal or healthy state relative to a control population, as described above, may be determined as progressing towards a healthy physiologic state. Furthermore, the rate at which the patient's characteristic data changes over time may indicative of a normal or abnormal, healthy or unhealthy physiologic state. For example, a rapid change in a patient's ischemic responses trending toward an abnormal or unhealthy state may be indicative of a more serious underlying disease or defect than would a more gradual change. Thus, while consecutive measurements of the patient's ischemic response may be within normal or healthy ranges, a trend in changes in the ischemic response or the rate at which the ischemic response is changing may be indicative of an abnormal or unhealthy state.

In another embodiment, the present invention provides a software program for characterizing a patient's oxygenation capabilities. A software program may be provided for controlling the operation of the sensor 14 and restriction means 12 as well as for inputting measurement data, determining characterizing data, and generating a display of patient data. Such a software program may be installed on a personal computer, processor, or other hardware as is commonly found in hospital and emergency rooms.

Figure 14:
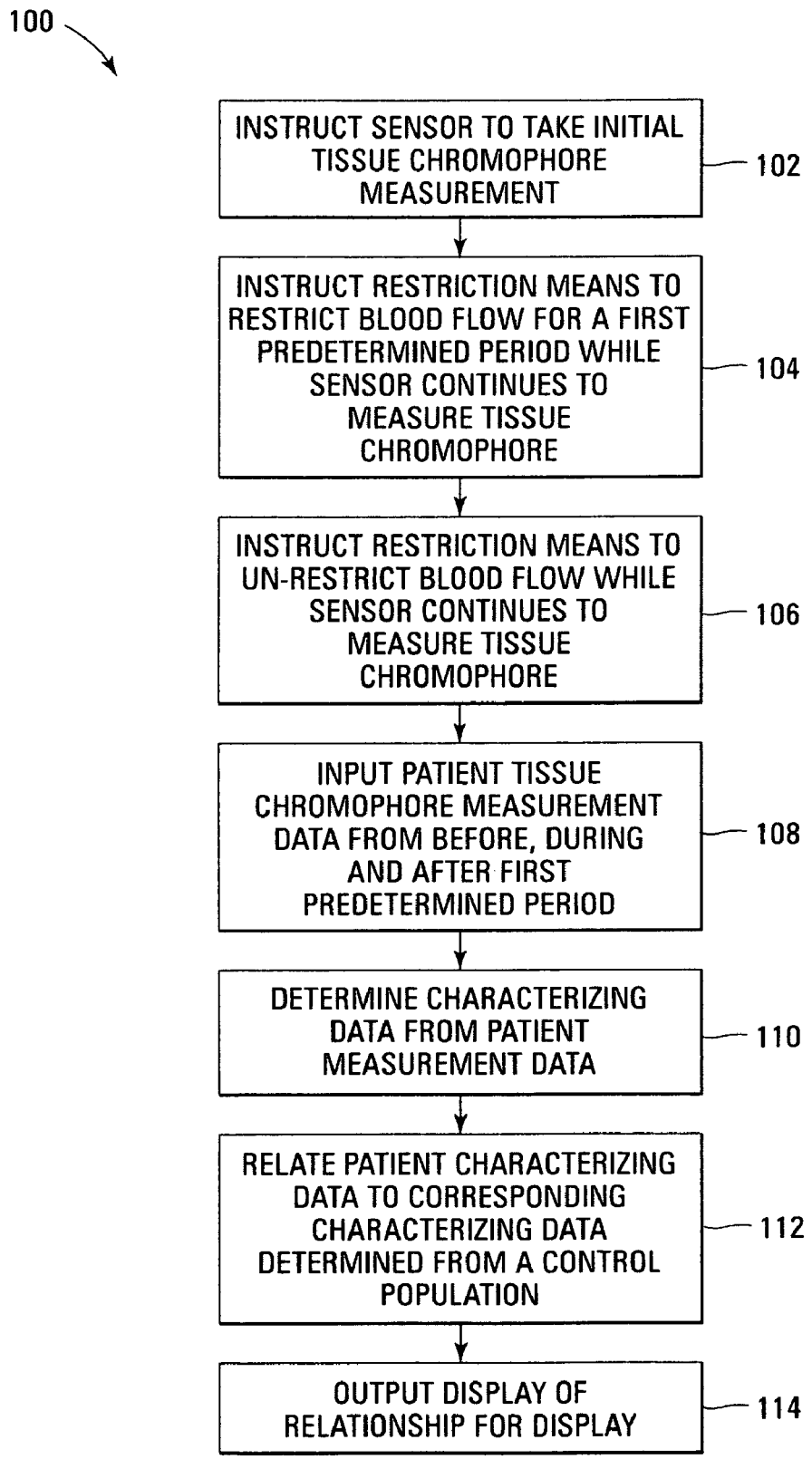
FIG. 14 is a flowchart illustrating the structure of a software program for use with an embodiment of the invention.

FIG. 14 outlines the structure of a software program 100 for use with an embodiment of the present invention. The software program instructs the sensor 14 to take an initial measurement of a tissue chromophore whose light absorption properties depend on the oxygenation state of the tissue (block 102). The software program 100 instructs the restriction means 12 to restrict blood flow to the tissue for a first predetermined period while the sensor 14 continues to measure the tissue chromophore (block 104). The software program 100 instructs the restriction means 12 to un-restrict blood flow to the tissue while the sensor 14 continues to measure the tissue chromophore (block 106). Patient tissue chromophore measurement data is inputted from before, during and after the first predetermined period (block 108). Characterizing data is determined from the patient measurement data (block 110) according to the methods previously described. The patient characterizing data is related to corresponding characterizing data determined from a control population (block 112) according to methods previously described. A display of the relationship is outputted for display on a monitor or other display means (block 114).

In another embodiment, the present invention is a software program adapted for determining characterizing data from inputted patient tissue chromophore measurement data (blocks 108 and 110).

A software program in accordance with the above-described embodiments may be further adapted to classify the patient's ischemic response based upon a comparison to a control population or in relation to changes in ischemic response over time. The software program may additionally be adapted to create a graphical display of the patient tissue chromophore data and/or characterizing data in relation to the corresponding data of the control population for display on the display 18.

System 10 provides an automatic method of converting raw data relating to a tissue chromophore into characterizing data, comparing the patient's characterizing data to corresponding characterizing data of a control population and classifying the patient's physiologic state based upon this comparison. System 10 substantially reduces the time and effort involved in making tedious and time consuming conversions and comparisons by hand. Furthermore, system 10 may be employed to reduce mistakes which may be made anytime such conversions and comparisons are performed by hand. In addition, system 10, when used in conjunction with an automatically-operating restriction means 12, may be used without requiring additional personnel.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method for analyzing data related to tissue oxygenation, in an apparatus including a processor, comprising the steps of:
   taking an initial measurement to collect data on a tissue chromophore whose light absorption properties depend on the oxygenation state of the tissue;
   controlling the operation of a restriction means to restrict blood flow for a first predetermined period in the region where the initial measurement was made while continuing to measure the tissue chromophore;
   controlling the operation of the restriction means to un-restrict the blood flow after the first predetermined period while continuing to measure the tissue chromophore; and
   with the processor:
   using the data collected during the measurements, automatically determining within the data an ischemia start point and an ischemia end point of the first predetermined period;
   wherein the step of determining within the data an ischemia end point comprises:
   transforming the data into second derivative points of the tissue chromophore measurement;
   identifying peaks in the data by identifying second derivative points that exceed an average of local second derivative points by a first predetermined amount;
   identifying valleys in the data by identifying second derivative points that are less than an average of local second derivative points by a second predetermined amount;
   identifying peaks that precede valleys within a predetermined time interval to determine a valid peak; and
   producing a correlation coefficient based on the second derivative points between each valid peak and its related valley versus the actual second derivative data.

2. The method of claim 1, wherein the step of determining within the data an ischemia end point further comprises:
   smoothing the data;
   producing the correlation coefficient by generating a curve fitting on the second derivative points between each valid peak and its related valley;
   comparing the correlation coefficient to a predetermined threshold;
   determining that the valley represents the ischemia end point if a first predetermined relationship exists between the correlation coefficient and the predetermined threshold; and
   determining that the valley does not represent the ischemia endpoint otherwise.

3. The method of claim 2, wherein the step of determining within the data an ischemia start point further comprises identifying a data point that precedes the ischemia end point by the first predetermined period.

4. The method of claim 3, comprising the further steps of:
   selecting data points occurring in a second predetermined time period after the ischemia start point;
   generating a curve fitting on the selected data points;
   selecting from time or a measurement number a value to use as an independent variable; and
   generating a correlation coefficient representative of a slope of onset of ischemia.

5. The method of claim 3, comprising the further steps of:
   for a time interval beginning at the ischemia start point and ending at the ischemia end point, fitting the data points to a non-linear exponential response curve equation of $CA_{fit}=(a_1+b_1*\{1-\exp[(-time+b_2)/b_3]\})$ where $CA_{fit}$=fitted data points, $a_1$=baseline data point value just before the ischemia start point, $b_1$=minimum data point value occurring between the ischemia start point and the ischemia end point minus $a_1$, $b_2$=time delay between the ischemia start point and when the data points in the time interval begin a significant decrease, and $b_3$=0.633; and determining the elapsed time between ($a_1$) and ($a_1$+EQ [minimum($CA_{fit}$)–$a_1$]) where EQ represents a fraction equilibrium time between 0 and 1; and for EQ=0.95 the resultant elapsed time is the 95% equilibrium response time for the tissue chromophore amount to reach an ischemia minimum, which is representative of an ischemia onset time.

6. The method of claim 2, comprising the further step of determining a recovery maximum point by identifying a maximum data point following the ischemia endpoint.

7. The method of claim 6, comprising the further step of determining a recovery end point by identifying a minimum data point occurring after the recovery maximum point.

8. The method of claim 7, comprising the further steps of:
selecting data points occurring between the ischemia end point and the recovery end point;
generating a curve fitting on the selected data points;
selecting from time or a measurement number a value to use as an independent variable; and
generating a correlation coefficient representative of a slope of recovery from ischemia.

9. The method of claim 7, comprising the further steps of:
identifying a minimum data point occurring between the recovery maximum point and the recovery end point; and
integrating the data points occurring in a time interval between the ischemia end point and the recovery end point for data points greater than the minimum data point.

10. The method of claim 6, comprising the further steps of:
for a time interval beginning at the ischemia end point and ending at the recovery maximum point, fitting data points to a non-linear exponential response curve equation $CA_{fit}=(a_1+c_1*\{1-\exp[(-time+c_2)/c_3]\})$, where $CA_{fit}$=fitted data points, $a_1$=baseline data point just before the ischemia start point, $c_1$=maximum tissue chromophore value occurring between the ischemia endpoint and the recovery maximum point minus $a_1$, $c_2$=time delay between ischemia start point and when data points in the time interval begin a significant increase, and $c_3$=0.633; and
determining an elapsed time between ($a_1$) and ($a_1$+EQ [maximum($CA_{fit}$)–a1]) where EQ represents a fraction equilibrium time between 0 and 1; and for EQ=0.95 the resultant elapsed time is the 95% equilibrium response time for the tissue chromophore amount to reach its maximum recovery point which is representative of an ischemia recovery time.

11. The method of claim 1, wherein the tissue chromophore is one of $StO_2$, oxyhemoglobin, deoxyhemoglobin and total hemoglobin in the tissue.

12. The method of claim 1, comprising the further step of adjusting the data by a total amount of hemoglobin in the patient's tissue.

13. A method of analyzing a patient's tissue oxygenation capabilities, in an apparatus including a processor, comprising the steps of:
measuring a tissue chromophore whose light absorption properties depend on an oxygenation state of the tissue and generating data representative of the patient's tissue oxygenation before, during and after a controlled ischemia event; and
automatically with the processor determining from said data patient characterizing data related to tissue oxygenation, the determining step further comprising:
selecting data points occurring between an ischemia end point and a recovery end point;
generating a curve fitting on the selected data points;
selecting from time or a measurement number a value to use as an independent variable; and
generating a correlation coefficient representative of a slope of recovery from ischemia.

14. The method of claim 13, wherein the tissue chromophore is one of $StO_2$, oxyhemoglobin, deoxyhemoglobin and total amount of hemoglobin in the tissue.

15. The method of claim 13, comprising the further step of displaying at least one of said tissue oxygenation measurement data and patient characterizing data on a display.

16. The method of claim 13, comprising the further step of determining a relationship between said patient characterizing data and corresponding characterizing data determined from a control population.

17. The method of claim 16, comprising the further step of displaying said relationship on a display.

18. The method of claim 17, wherein the relationship is displayed as a distribution meter plot in which the control population characterizing data is fit to a distribution curve.

19. The method of claim 18, wherein the distribution curve is a log normal probability density function.

20. The method of claim 18, wherein said patient characterizing data is plotted on the distribution curve showing the patient characterizing data relative to a distribution center and spread of the control population characterizing data.

21. The method of claim 20, wherein the distribution center and spread of the control population characterizing data is one of mean or median and standard deviation or percentile.

22. The method of claim 17, wherein the relationship is displayed as a distribution statistic trend plot in which the patient characterizing data is scatter plotted or line graphed versus time.

23. The method of claim 22, wherein the distribution statistic trend plot shows the distance of patient characterizing data relative to a distribution of the control population characterizing data.

24. The method of claim 23, wherein the distribution position includes one of percentile, t, z or f value, p-value, curve area left or right of the patient characterizing data, difference between patient characterizing data and control population mean, or standard deviation.

25. The method of claim 17, wherein the relationship is displayed as an analysis trend plot relative to the control population characterizing data.

26. The method of claim 17, wherein the patient characterizing data is plotted on a scatter plot or a line graph versus time with normal limits shown as constant lines representing the center and spread of the control population characterizing data.

27. The method of claim 16, wherein the control population is known to be healthy.

28. The method of claim 16, wherein the control population is known to be unhealthy.

29. The method of claim 16, wherein the control population shares at least a first selected attribute of the patient.

30. The method of claim 29, wherein the at least first selected attribute is one of sex, age range, weight range or health attribute.

31. The method of claim 16, comprising the further steps of determining that an ischemic response of the patient is normal if a first predetermined relationship exists between the patient characterizing data and the control population characterizing data and determining that the patient ischemic response is abnormal otherwise.

32. The method of claim 31, wherein the first predetermined relationship comprises the patient characterizing data being within about the $5^{th}$ to the $95^{th}$ percentile of the control population characterizing data.

33. The method of claim 31, wherein the first predetermined relationship comprises the patient characterizing data being within about two standard deviations of the control population characterizing data.

34. The method of claim 16, comprising the further steps of determining that an ischemic response of the patient is healthy if a first predetermined relationship exists between the patient characterizing data and the control population characterizing data and determining that the patient ischemic response is unhealthy otherwise.

35. The method of claim 34, wherein the first predetermined relationship comprises the patient characterizing data being within about the $5^{th}$ to the $95^{th}$ percentile of the control population characterizing data.

36. The method of claim 34, wherein the first predetermined relationship comprises the patient characterizing data being within a range of two standard deviations of the control population characterizing data.

37. The method of claim 13, comprising the further step of repeating the method periodically for an extended period of time.

38. The method of claim 13, comprising the further step of indicating when patient characterizing data is outside of a pre-determined range of values.

39. The method of claim 38, wherein the step of indicating further comprises the step of indicating by at least one of audible, visual or sensory signals.

40. The method of claim 13, wherein the characterizing data is one of ischemia onset slope, ischemia onset response time, ischemia recovery slope, ischemia recovery response time or hyperemia.

41. The method of claim 13, wherein determining from said data characterizing data related to tissue oxygenation further comprises a step of adjusting said characterizing data by the total amount of hemoglobin in the patient's tissue.

42. A method of analyzing a patient's tissue oxygenation capabilities, in an apparatus including a processor, comprising the steps of:
measuring a tissue chromophore whose light absorption properties depend on an oxygenation state of the tissue; and
generating data representative of the patient's tissue oxygenation before, during and after a controlled ischemia event; and
with the processor automatically determining from said data characterizing data related to tissue oxygenation, wherein determining from said data characterizing data related to tissue oxygenation comprises the further steps of:
selecting data points occurring in a predetermined time period after an ischemia start point;
generating a curve fitting on the selected data points;
selecting from time or a measurement number a value to use as an independent variable; and
generating a correlation coefficient representative of a slope of onset of ischemia.

43. A method of analyzing a patient's tissue oxygenation capabilities, in an apparatus including a processor, comprising the steps of:
measuring a tissue chromophore whose light absorption properties depend on an oxygenation state of the tissue; and
generating data representative of the patient's tissue oxygenation before, during and after a controlled ischemia event; and with a processor
automatically determining from said data characterizing data related to tissue oxygenation, wherein determining from said data characterizing data related to tissue oxygenation comprises the flirt her steps of:
for a time interval beginning at an ischemia start point and ending at an ischemia end point, fitting the data points to a non-linear exponential response curve equation of $CA_{fit}=(a_1+b_1*\{1-\exp[(-time+b_2)/b_3]\})$ where $CA_{fit}$=fitted data points, $a_1$=baseline data point value just before the ischemia staff point, $b_1$=minimum data point value occurring between the ischemia start point and the ischemia end point minus $a_1$, $b_2$=time delay between the ischemia start point and when the data points in the time interval begin a significant decrease, and $b_3$=0.633; and
determining the elapsed time between $(a_1)$ and $(a_1+EQ[minimum(CA_{fit})-a_1])$ where EQ represents a fraction equilibrium time between 0 and 1; and for EQ=0.95 a resultant elapsed time is the 95% equilibrium response time for the tissue chromophore amount to reach an ischemia minimum, which is representative of an ischemia onset time.

44. A method of analyzing a patient's tissue oxygenation capabilities, in an apparatus including a processor, comprising the steps of:
measuring a tissue chromophore whose light absorption properties depend on an oxygenation state of the tissue; and
generating data representative of the patient's tissue oxygenation before, during and after a controlled ischemia event; and
with a processor automatically determining from said data characterizing data related to tissue oxygenation wherein determining from said data characterizing data related to tissue oxygenation comprises the flirt her steps of:
for a time interval beginning at an ischemia end point and ending at a recovery maximum point, fitting data points to a non-linear exponential response curve equation $CA_{fit}=(a_1+c_1*\{1-\exp[(-time+c_2)/c_3]\})$, where $CA_{fit}$=fitted data points, $a_1$=baseline data point just before an ischemia start point, $C_1$=maximum tissue chromophore value occurring between the ischemia endpoint and recovery maximum point minus $a_1$, $C_2$=time delay between the ischemia start point and when data points in the time interval begin a significant increase, and $c_3$=0.633; and
determining an elapsed time between $(a_1)$ and $(a_1+EQ[maximum(CA_{fit})-a_1])$ with EQ representing a fraction equilibrium time between 0 and 1; and for EQ=0.95 the resultant elapsed time is the 95% equilibrium response time for the tissue chromophore amount to reach its maximum recovery point which is representative of an ischemia recovery time.

45. A method of analyzing a patient's tissue oxygenation capabilities, in an apparatus including a processor, comprising the steps of:

measuring a tissue chromophore whose light absorption properties depend on an oxygenation state of the tissue; and generating data representative of the patient's tissue oxygenation before, during and after a controlled ischemia event; and with a processor automatically determining from said data characterizing data related to tissue oxygenation, wherein determining from said data characterizing data related to tissue oxygenation comprises the further steps of:

determining a recovery maximum point and a recovery end point;

identifying a minimum data point occurring between the recovery maximum point and the recovery end point; and integrating the data points occurring in a time interval between an ischemia end point and the recovery end point for data points greater than the minimum data point.

46. An apparatus for analyzing a patient's tissue oxygenation capabilities, the apparatus comprising:

a software program on a storage medium, wherein the software program is adapted to perform the following process:

input data from measurements of a tissue chromophore whose light absorption properties depend on the oxygenation state of the tissue before, during and after a controlled ischemic event;

determine from said data patient characterizing data related to tissue oxygenation;

select data points occurring between an ischemia end point and a recovery end point;

generate a curve fitting on the selected data points;

select from time or a measurement number a value to use as an independent variable; and generate a correlation coefficient representative of a slope of recovery from ischemia.

47. The apparatus of claim 46, wherein the characterizing data is one of ischemia onset slope, ischemia onset response time, ischemia recovery slope, ischemia recovery response time and hyperemia.

48. The apparatus of claim 46, wherein the software program is further adapted to determine a relationship between said patient characterizing data and corresponding characterizing data determined from a control population.

49. The apparatus of claim 48, wherein the software program is further adapted to determine that an ischemic response of the patient is normal if a predetermined relationship exists between the patient characterizing data and the corresponding characterizing data of the control population and determine that the patient ischemic response is abnormal otherwise.

50. The apparatus of claim 48, wherein the software program is further adapted to determine that an ischemic response of the patient is normal if a predetermined relationship exists between the patient characterizing data and the corresponding characterizing data of the control population and determine that the patient ischemic response is unhealthy otherwise.

51. The apparatus of claim 48, wherein the software program is further adapted to generate a display of said relationship.

\* \* \* \* \*

UNITED STATES PATENT AND TRADEMARK OFFICE
CERTIFICATE OF CORRECTION

PATENT NO.         : 7,536,214 B2
APPLICATION NO.    : 11/259382
DATED              : May 19, 2009
INVENTOR(S)        : Dean E. Myers et al.

Page 1 of 1

It is certified that error appears in the above-identified patent and that said Letters Patent is hereby corrected as shown below:

Page 2, Col. 2, line 13, Other Publications, insert
--FANTINI et al., "Spatial Mapping of Blood Flow and Oxygen Consumption in the Human Calf Muscle Using Near-Infrared Spectroscopy", Bioengineering Center, Department of Electrical Engineering and Computer Science, Tufts University, Medford, Massachusetts, 8 pages--

Column 20, line 3: after "ischemia event; and" insert --with the processor:--
Column 20, line 4: after "automatically" delete "with the processor"

Column 21, line 45: replace "the" first occurrence with --a--

Column 22, line 9: after "with a processor" insert --:--
Column 22, line 13: replace "flirt her" with --further--
Column 22, line 41: after "with a processor" insert --:--
Column 22, line 42: after "oxygenation" insert --,--
Column 22, line 51: replace "$C_1$" with --$c_1$--
Column 22, line 54: replace "$C_2$" with --$c_2$--

Column 23, line 7: after "with a processor" insert --:--

Column 24, line 23: replace "normal" with --healthy--
Column 24, line 26: after "and" insert --to--

Signed and Sealed this

Fourteenth Day of July, 2009

JOHN DOLL
*Acting Director of the United States Patent and Trademark Office*